(12) United States Patent
Mitchell et al.

(10) Patent No.: US 10,488,379 B2
(45) Date of Patent: Nov. 26, 2019

(54) UNIFORMITY INDEX PERFORMANCE EVALUATION IN AN SCR AFTERTREATEMENT SYSTEM

(71) Applicant: Cummins Emission Solutions Inc., Columbus, IN (US)

(72) Inventors: Douglas A. Mitchell, Indianapolis, IN (US); Tamas Szailer, Clarkston, MI (US); Alonzo Scott Cole, Columbus, IN (US); Newton Crenshaw, Zionsville, IN (US)

(73) Assignee: Cummins Emission Solutions Inc., Columbus, IN (US)

( * ) Notice: Subject to any disclaimer, the term of this patent is extended or adjusted under 35 U.S.C. 154(b) by 1039 days.

(21) Appl. No.: 14/431,698

(22) PCT Filed: Oct. 21, 2013

(86) PCT No.: PCT/US2013/065851
§ 371 (c)(1),
(2) Date: Mar. 26, 2015

(87) PCT Pub. No.: WO2014/066214
PCT Pub. Date: May 1, 2014

(65) Prior Publication Data
US 2015/0241400 A1    Aug. 27, 2015

Related U.S. Application Data

(60) Provisional application No. 61/717,560, filed on Oct. 23, 2012.

(51) Int. Cl.
*G01N 33/00* (2006.01)
*G01N 1/22* (2006.01)
(Continued)

(52) U.S. Cl.
CPC ...... *G01N 33/0037* (2013.01); *G01M 15/102* (2013.01); *G01N 1/2252* (2013.01);
(Continued)

(58) Field of Classification Search
None
See application file for complete search history.

(56) References Cited

U.S. PATENT DOCUMENTS

| 3,885,437 A | 5/1975 | Reagan |
| 2005/0016266 A1 | 1/2005 | Rabl |

(Continued)

FOREIGN PATENT DOCUMENTS

WO    WO-2011/048294    4/2011

OTHER PUBLICATIONS

International Search Report and Written Opinion for International Application No. PCT/US2013/065851, dated Mar. 21, 2014, 12 pages.

*Primary Examiner* — Bijan Mapar
(74) *Attorney, Agent, or Firm* — Foley & Lardner LLP

(57) ABSTRACT

An exemplary exhaust testing apparatus includes a housing defining an exhaust flow path extending from an inlet to an outlet. At least a portion of the housing is selectably rotatable relative to an exhaust aftertreatment system. An arm extends from the housing into the exhaust flow path. An exhaust probe configured to measure an exhaust constituent is coupled with the arm and positioned at a location in the exhaust flow path. An actuator is configured to extend and retract the arm to vary the location of the exhaust probe in the exhaust flow path. The exhaust probe is moveable to a plurality of locations within the exhaust flow path through a combination of rotation of the housing and extension and retraction of the arm.

14 Claims, 25 Drawing Sheets

(51) Int. Cl.
*G01M 15/10* (2006.01)
*G06F 17/10* (2006.01)
*G06F 17/50* (2006.01)
*F01N 11/00* (2006.01)
*F01N 3/10* (2006.01)
*F01N 3/20* (2006.01)

(52) U.S. Cl.
CPC .......... *G06F 17/10* (2013.01); *G06F 17/5009* (2013.01); *F01N 3/103* (2013.01); *F01N 3/2066* (2013.01); *F01N 11/00* (2013.01); *F01N 11/007* (2013.01); *F01N 2550/02* (2013.01); *Y02A 50/245* (2018.01)

(56) References Cited

U.S. PATENT DOCUMENTS

| | | | |
|---|---|---|---|
| 2007/0089501 A1* | 4/2007 | Endicott | G01M 15/102 73/114.71 |
| 2007/0240490 A1* | 10/2007 | Desrochers | G01N 1/26 73/31.01 |
| 2009/0272102 A1 | 11/2009 | Ofoli et al. | |
| 2011/0179769 A1* | 7/2011 | Zhang | F01N 11/00 60/273 |

* cited by examiner

UNIFORMITY INDEX PERFORMANCE EVALUATION IN AN SCR AFTERTREATEMENT SYSTEM

CROSS REFERENCE TO RELATED APPLICATIONS

The present application is a U.S. National Stage of PCT Patent Application No. PCT/US2013/065851, filed Oct. 21, 2013, which claims the benefit of priority to U.S. Provisional Application No. 61/717,560, filed on Oct. 23, 2012. The contents of the aforementioned applications are incorporated herein by reference in their entirety.

BACKGROUND

The technical field generally relates to aftertreatment control of emissions in internal combustion engines, and more specifically but not exclusively relates to design and modeling of aftertreatment catalytic systems.

Selective catalytic reduction (SCR) systems depend upon the injection of ammonia or urea, or sometimes an alternate reductant such as hydrocarbons, into the system. The injected reductant processes in the exhaust gas, ultimately entering the gas phase and adsorbing to the catalyst surface for reaction with adsorbed $NO_x$ from the engine. The reductant may have to experience evaporation, hydrolysis or other decomposition, and adsorption. The resulting exhaust gas composition can be variable across the exhaust system cross-section, resulting in variability in available reductant and in the ratio of reductant to $NO_x$ or other reactants.

SCR systems, and other aftertreatment systems, for mobile applications such as vehicles are highly sensitive to cost and packaging footprint. Catalyst sizing therefore is closely matched to capability, with the smallest catalyst having the lowest catalyst loadings that will meet the needs of the application being utilized. The needs of the application include accounting for part to part variability in manufacturing, degradation over time and events such as high temperature excursions or exposure to sulfur. The uniformity profile of injected and processed reductant is a part of the performance of the aftertreatment system, and designs having lower uniformity ultimately require relatively larger catalysts and/or catalyst loadings to meet the requirements of the application.

The determination of the uniformity is a challenging operation, and can require a large amount of design effort and numerous design iterations. Analytical solutions, such as computational fluid dynamics (CFD) operations allow multiple systems to be tested and adjusted more cheaply, but do not always match real systems. Presently known testing rigs for determining uniformity of exhaust gas constituents, and accordingly for calibrating a CFD design and/or for testing a physical design, require significant warm-up and preparation periods, allowing for only a few data point acquisitions each day. Therefore, further technological developments are desirable in this area.

SUMMARY

Unique apparatuses, methods and systems for exhaust aftertreatment system testing are disclosed. One exemplary apparatus includes at least one exhaust probe being moveable to a plurality of locations within a portion of a sectional area of an exhaust flow path defined in a housing through a combination of rotation of the housing and extension and retraction of an arm. One exemplary method includes performing a plurality of measurements of exhaust species concentration with a probe in a plurality of locations within a flow path of a test device where the probe is moveable to the plurality of locations by operating a linear actuator, rotating at least a portion of the test device, or a combination thereof. One exemplary system is configured to position a probe in a plurality of locations in an exhaust passage of a test device through movement of an extension member without interrupting exhaust flow in the exhaust passage. Further embodiments, forms, objects, features, advantages, aspects, and benefits shall become apparent from the following description and figures.

DESCRIPTION OF ILLUSTRATIVE EMBODIMENTS

Figure 1:
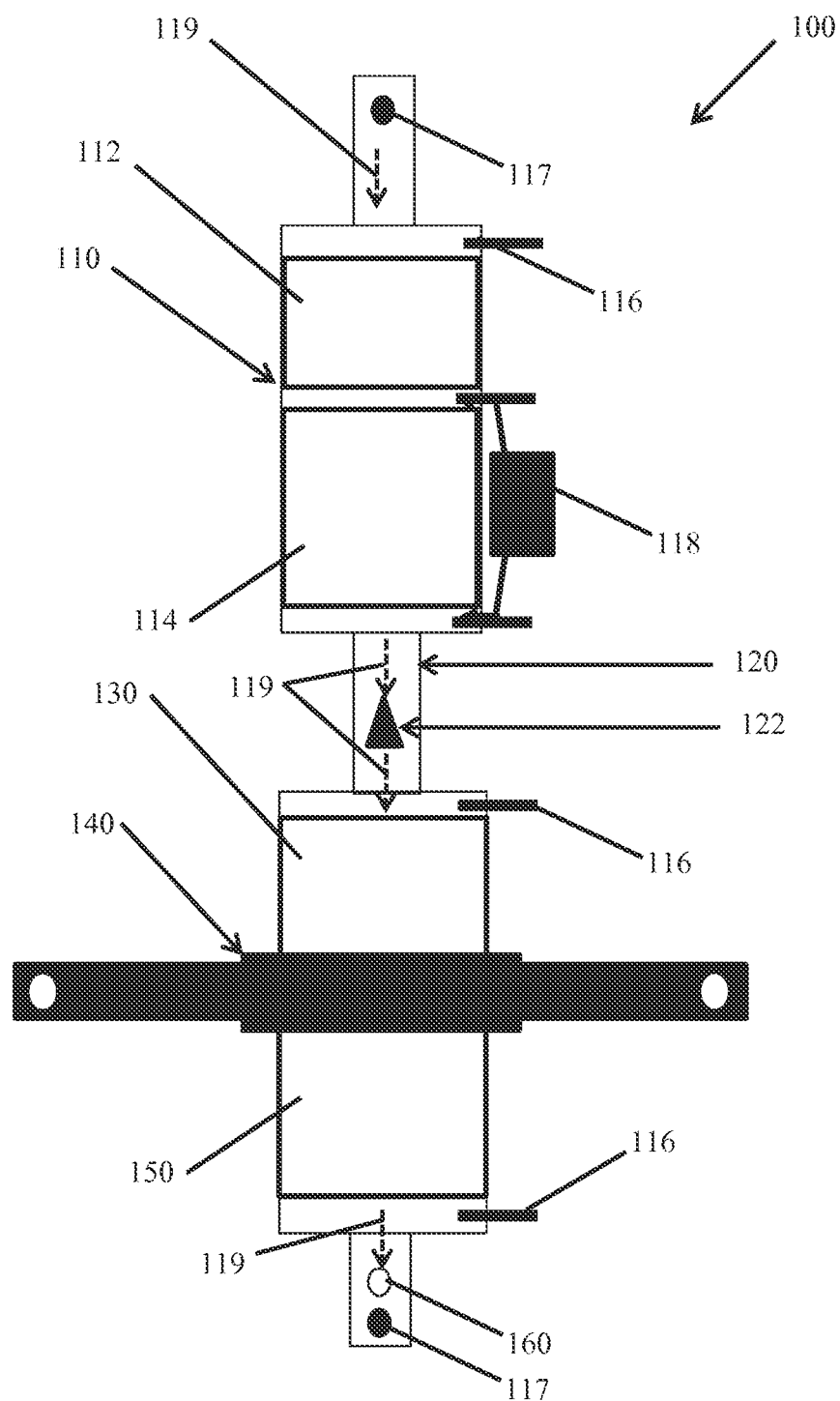
FIG. 1 illustrates an exemplary aftertreatment setup in test cell.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein.

A system is described that is capable of mapping gaseous species across the face of a catalyst under normal engine operating conditions without special venting mechanisms or substantially changing the flow characteristics within the system. This occurs without significant operator intervention and drastically improves, by several orders of magnitude, the time needed to conduct a similar survey from previously known systems.

Current CFD techniques have not adequately captured the complex fluid, heat transfer, and species mechanics necessary to map out the capability of a system to spread a reductant evenly. Additionally, current systems can only sample in predetermined static locations or they must vent into the atmosphere which can create environmental and health considerations. The described system overcomes one or more of these deficiencies by experimentally obtaining the necessary information to map out and analyze these interactions. This capability can then be used, for example, to design and optimize mixers, inlets, outlets, total system integration, and/or test or improve CFD models.

In certain embodiments, all of the parts are designed to be robust to high temperatures, or actively cooled, and can accommodate on engine experimentation for exhaust temperatures up to 575° C. The inclusion of high temperatures parts and/or cooling is optional, and dependent upon the temperatures of interest for the system. Systems capable of withstanding exhaust temperatures higher or lower than 575° C. are also contemplated herein.

In certain embodiments, the sampling probes are actively heated once they pass out of a sealed area to prevent $NH_3$, urea, unburned hydrocarbons, or other gas constituents from sticking to their lines. An exemplary system includes probe entrances sealed to prevent gases from venting into the atmosphere. The system includes probes mounted on extension arms which are coupled with linear actuators so that programmable locations can be sampled to increase the radial and/or angular resolution of sampling across the catalyst face. The selection of the distance between the probes and the extension length available for the actuators allows for rapidly deployable and arbitrarily selectable configurations of sampling locations. The sampling locations can be programmed or dynamically calculated based upon the user need, and can be performed through an automated cycle and/or by sequential positioning. The positioning may be manually or computer controlled.

With reference to FIG. 1, there is illustrated a system 100 including an exemplary aftertreatment setup in a test cell. System 100 was utilized in emissions testing performed on a Cummins EPA 2013 ISB 6.7 L engine. An EPA 2013 compliant aftertreatment system was used after the engine to maintain system backpressure equivalent to an actual system. The exhaust from turbine out was passed through a DOC/DPF system 110 including a diesel oxidation catalyst (DOC) 112 and a diesel particulate filter (DPF) 114. The direction of exhaust flow through system 100 is generally illustrated by arrows 119. System 100 further includes temperature sensors 116, $NO_x$ sensors 117, delta P+P pressure sensors 118, and Fourier transform infrared spectroscopy (FTIR) sampling probe 160.

From DOC/DPF system 110, exhaust passes into a decomposition reactor tube 120. An aqueous urea solution of diesel exhaust fluid (urea-based DEF) was dosed in decomposition reactor tube 120 through a doser 122 and converted into $NH_3$. The exhaust flow mixed with $NH_3$ was then passed through a hydrolysis catalyst 130 to ensure that all liquid urea was converted to $NH_3$ before the emissions measurement. The SUMS (Species Uniformity Measurement System) system 140 was installed after the hydrolysis catalyst 130 to measure the exhaust species concentration. FTIR sampling probes of the SUMS system 140 were connected to an FTIR system which provided raw species concentrations. Further details of SUMS system 140 are described below in connection with FIG. 2.

It shall be appreciated that certain embodiments omit a hydrolysis catalyst. Such embodiments may inject reductant and allow it to go through a shortened selective catalytic reduction before making a measurement. Rather than measuring $NH_3$ and HNCO directly, such embodiments may utilize upstream emissions measurements and emissions measurements of the SUMS to calculate how much reductant was consumed by the SCR catalyst during $NO_x$ conversion and then back calculate how much reductant was traveling through a given zone.

An un-catalyzed SCR brick 150 was installed after the SUMS system 140 to make sure that the back pressure equivalent to an operating system was obtained. The SCR brick 150 was un-catalyzed to ensure that $NO_x$ was not reduced by $NH_3$ before the emissions measurement in the tail-pipe. The size of the SCR brick 150 was determined such that the total volume of the SCR system (hydrolysis catalyst 130+un-catalyzed SCR brick 150) was equivalent to a production SCR system. An additional FTIR sampling probe 160 was connected at a sufficient distance downstream of the tailpipe to get a well-mixed measurement of the exhaust species. Periodic leak check and system accuracy tests were performed on the FTIR system to ensure quality and integrity of data. Exhaust temperatures were measured at the locations of temperature sensors 116 in the aftertreatment system illustrated in FIG. 1. The engine and dynamometer were operated through a scheduled sequence to run the engine at the required test conditions.

Figure 2:
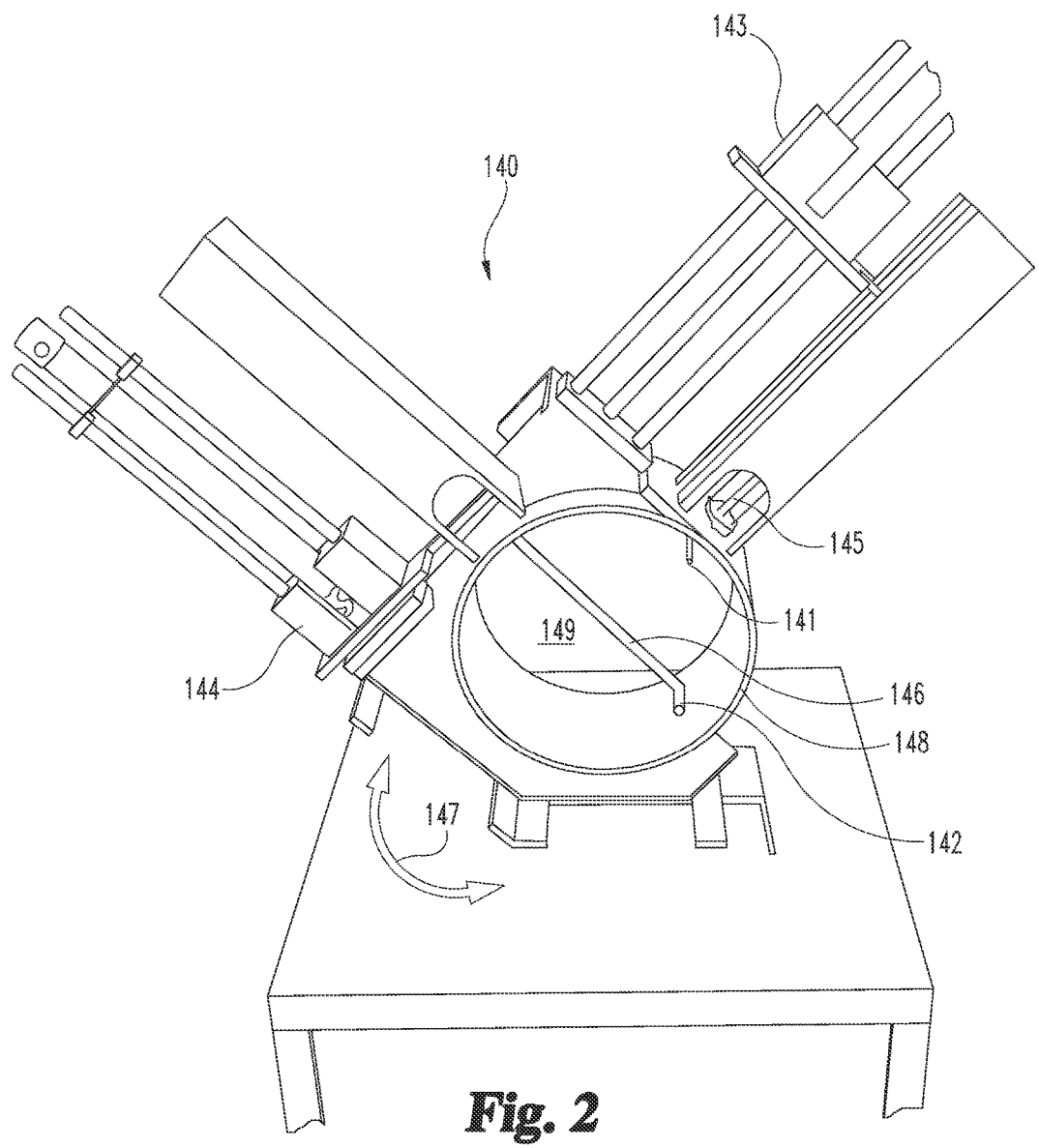
FIG. 2 illustrates an exemplary species uniformity measurement system (SUMS).

With reference to FIG. 2 there is illustrated an exemplary species uniformity measurement system (SUMS) 140. FIG. 2 depicts SUMS 140 in the form of a sampling disk that is configured to be installed in an exhaust system at a desired location, for example downstream of a catalyst as illustrated in FIG. 1. The sampling disk of SUMS 140 includes a housing 148 which defines an exhaust flow passage 149. The inlet and outlet ends of housing 148 may be coupled with respective first and second portions of an exhaust aftertreatment system, for example, as illustrated in FIG. 1. SUMS 140 further includes FTIR sampling probes 141 and 142 which are coupled with extension arms 145 and 146 respectively. Extension arms 145 and 146 are operatively coupled with linear actuators 143 and 144, respectively. Linear actuators 143 and 144 are configured to extend and retract extension arms 145 and 146 effective to move probes 141 and 142 to different locations across the sectional area of the exhaust flow passage 149. This movement allows probes 141 and 142 to sample at different locations laterally across the face of an aftertreatment component with minimal intervention and disruption.

In the configuration illustrated in FIG. 2, probe 141 is illustrated in a nearly fully retracted position and probe 142 is illustrated in a nearly fully extended position. SUMS 140 is also rotatable in about its axis generally in the direction indicated by arrow 147 which allows probes 141 and 142 to sample at different locations circumferentially around face of the SCR brick 150 with minimal intervention and disruption. A rotation range of at least about 90 degrees in combination with the range of the linear actuators 143 and 144 provides effective sample location coverage of substantially the entire face of the SCR brick 150. Linear actuators 143 and 144 and rotation of the SUMS 140 allow positioning the sampling probe at substantially any cross-sectional location of exhaust flow passage 149 without a shutdown or other interruptions of engine operation. Exemplary sets of test locations are illustrated in graphs 301 and 302 of FIG. 3 both of which depict units of inches on their vertical and horizontal axes.

During the aforementioned linear movement and rotation SUMS 140 can function under normal operating engine conditions including during active regeneration events. Exhaust gases are prevented from venting into the testing space during operation. SUMS 140 can be controlled with a programmable controller to sample across a catalyst face in a predetermined or a dynamic location based upon various inputs. The design of SUMS 140 is easily modified for different size catalysts. SUMS 140 can also be instrumented with various tools, including thermocouples, pressure sensors, hot wire anemometers, to name several examples.

Using SUMS 140, species may be mapped as a function of location which is highly useful information for system design and integration.

Figure 3:
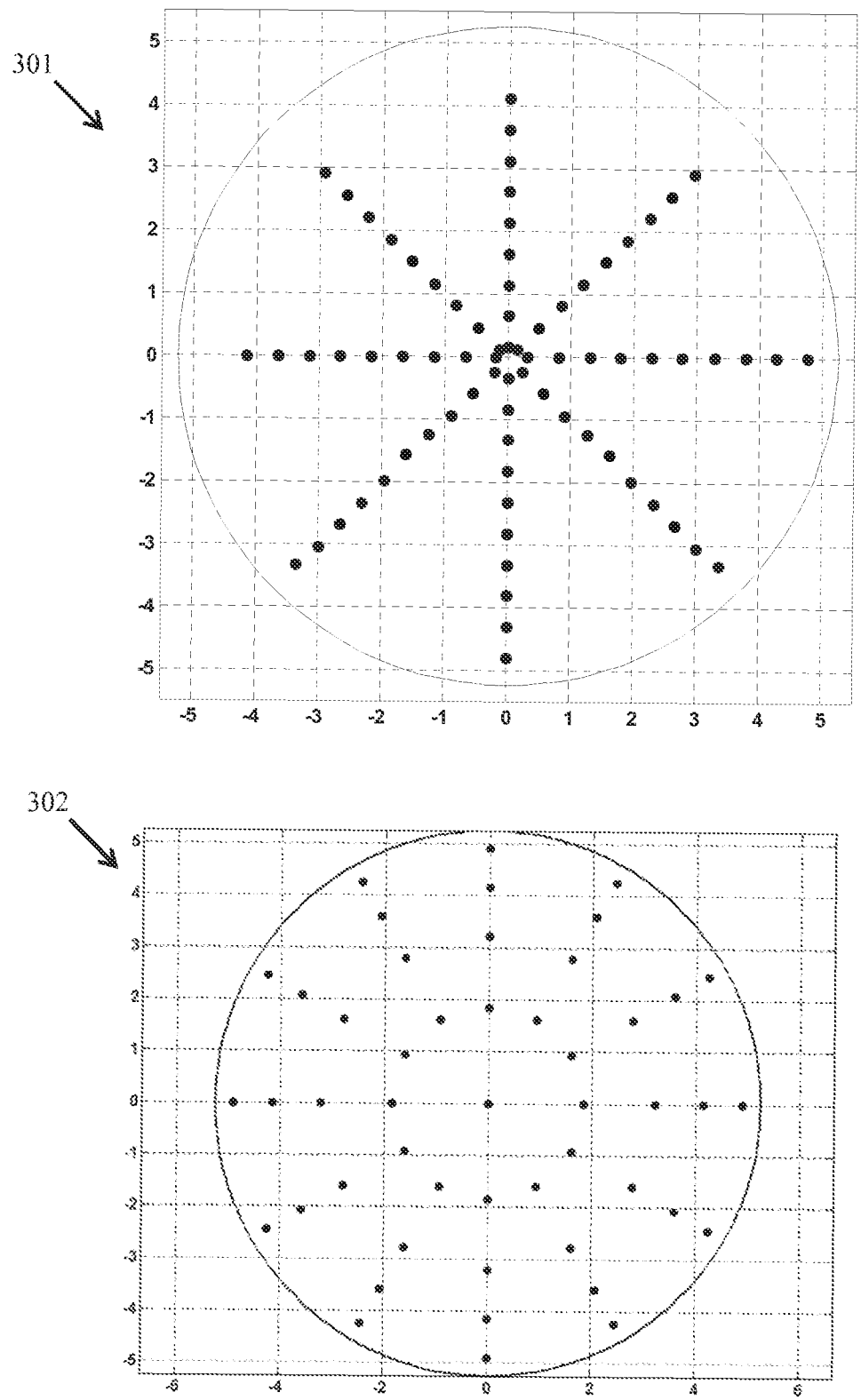
FIG. 3 illustrates graphs of exemplary grid of locations that may be sampled with a SUMS.
Figure 4:
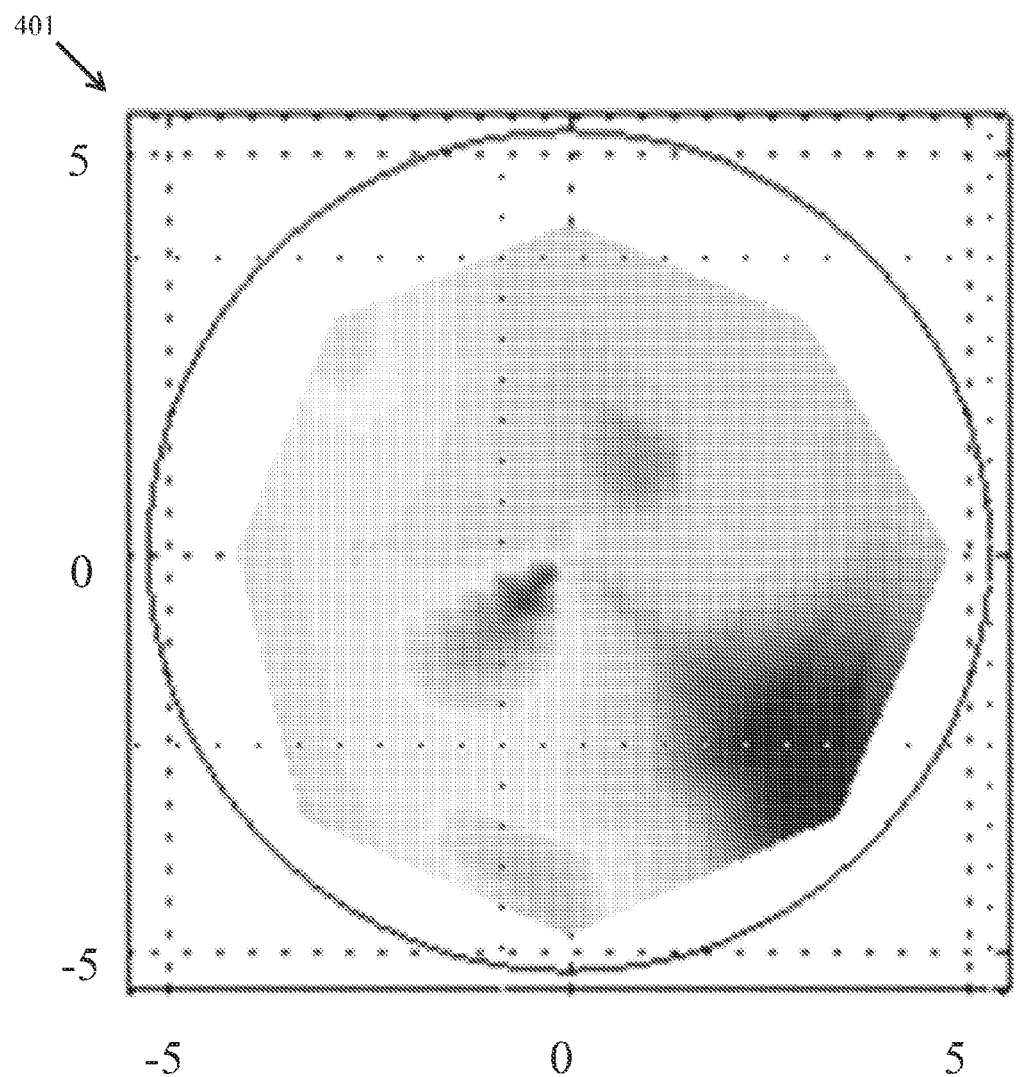
FIG. 4 illustrates a map of species across a catalyst face obtained using a SUMS.

Map 401 illustrated in FIG. 4 was created in two days using the test points illustrated in graph 301 of FIG. 3. Map 401 depict units of inches on its vertical and horizontal axes. Additional radial resolution was found to be unnecessary based on the test results, but it can be seen that additional or alternate points and better radial resolution is possible if desired. Graph 302 of FIG. 3 provides one illustration of an alternate set of test points. All points were mapped at three separate engine conditions within the two day period. It is estimated that conventional test systems would have taken between 54 and 72 days to provide an equivalent amount of data. Conventional systems required thirty minutes per point, then test cell shutdown, an operator adjustment of the sampling locations, an engine restart, stabilization to steady state operation, and then re-measurement. Experience with conventional test systems showed that about three to four operating points could be acquired per day.

Description of an example test of a CFD utilizing SUMS 140 in the system 100 follows. The system and data taken in the described example provides an example of a system and demonstrates the type of data available from, and usage of, the described system. The same or similar tests or operations are readily performed by one of skill in the art having the benefit of the present disclosure.

Selective Catalytic Reduction of oxides of nitrogen ($NO_x$) by ammonia has established itself as an effective diesel aftertreatment technology to meet stringent $NO_x$ emission standards. For satisfactory performance, good mixing between reductant and $NO_x$ needs to be achieved within tight packaging constraints and typically a uniformity index (UI) is used to quantify the degree of mixing. A primary objective of the disclosed testing was to compare experimentally measured and CFD predicted uniformity indices in realistic aftertreatment systems and to establish the correlation between them.

A measurement system, including hardware consistent with the SUMS 140 depicted in FIG. 2 was used to measure spatial distributions of ammonia and $NO_x$ at the outlet of a hydrolysis catalyst and to thus derive the experimental UI. Grid locations for measurement were chosen using the equal area method. In addition, UI was predicted through CFD simulations using a multi-component model that accounts for spray processes, water vaporization and urea thermolysis. Synchronized data flow was established between CFD and test-cell to ensure the conditions matched in both studies. Comparisons were made between experimentally measured and predicted UIs for 5 different configurations (9 cases), and the correlation was established. Main sources of uncertainties in measurements and predictions were identified as further described below.

Steady state testing was performed to measure the emissions concentrations at different locations across the SCR catalyst face using the test cell aftertreatment setup of system 100 including SUMS system 140. Tests were conducted at B50 and C100 engine operating conditions. The B50 engine operating condition was selected since it represents the center point of the fuel map and is representative of cruising condition for an on highway application. The C100 engine operating condition was chosen because it represents a high temperature and high flow condition, which may be a challenging situation from a flow mixing and distribution point of view.

Grid points required to map the catalyst face for emissions measurements were selected based on the equal area method. A total of 48 points were chosen along with the center point. Data at center point was not included in the calculation of the uniformity index. The locations of the measurement points are illustrated in graph 302 of FIG. 3. Baseline orientation of the SUMS tool mapped the grid in the 0° and 90° directions with regards to the horizontal. The SUMS tool was then rotated twice by 30° each to map the remaining grid points. The center point was repeated in each orientation.

During the test, initially, both arms of the SUMS tool were pushed out such that the probes were at the rim of the catalyst. The engine was then controlled to achieve the required exhaust flow conditions. DEF dosing rate was controlled such that ammonia to $NO_x$ ratio (ANR) of 1 was maintained. Arm 1 of the SUMS tool was then moved to the location for point 1 on the grid. Sampling of emissions was started after 10 min running to ensure stability. Sample was collected for 5 min at a sampling rate of 1 Hz and the average value over 5 min was reported. DEF dosing was shut off at the end of sampling time of 5 min and arm 1 was pushed back out to the rim. The engine was then run at high speed and load conditions for 10 min to acquire high flow rate and high exhaust temperature. This was done to ensure that all residual $NH_3$ was removed from the system before the sample at the next grid location was collected. After 10 min were complete, the engine was controlled to achieve the required flow rate and temperature conditions (B50 or C100). Then arm 1 was moved to the second grid location. DEF dosing was started and after 10 min emissions sampling was started. This process was repeated for all of the 49 points on the grid. After the grid mapping test for each configuration was completed, the FTIR sampling probe was removed from the SUMS tool and installed in a location downstream of tailpipe out to measure the total average exhaust concentration.

The above mentioned test procedure was performed on five different configurations (9 cases) to develop the correlation between CFD predicted and experimentally measured UIs. The five configurations (9 cases) are outlined in Table 1 below. Eight cases were used to develop the correlation and case 9 was used to validate it.

TABLE 1

Experimental Test Configurations

| Case # | SCR Inlet configuration | Decomposition tube | Operating condition |
| --- | --- | --- | --- |
| 1 | End Inlet | EPA 2010 | B50 |
| 2 | End Inlet | EPA 2010 | C100 |
| 3 | End Inlet | EPA 2013 | B50 |
| 4 | End Inlet | EPA 2013 | C100 |
| 5 | Side inlet | EPA 2010 | B50 |
| 6 | Side Inlet | EPA 2010 | C100 |
| 7 | Side Inlet | EPA 2013 | B50 |
| 8 | Side Inlet | EPA 2013 | C100 |
| 9 | End Inlet with cyclone mixer | EPA 2013 | C100 |

Results and figures from the CFD work and experimental testing are illustrated in FIGS. 5-22. Emissions concentrations measured at each of the 49 locations were recorded and cubic interpolation was done to get surface distribution contour plots. Sufficient ANR distribution across the SCR catalyst face is desirable to achieve maximum $NO_x$ conversion efficiency from the SCR catalyst. Hence, ANR distribution across the SCR catalyst inlet face obtained from CFD is compared to the distribution obtained from experimental testing. The view in FIGS. 5-22 is from the upstream side, or looking at the SCR inlet catalyst face from the decomposition tube outlet to SCR inlet. It can be seen that data of the type seen in FIGS. 5-12, which can be taken in a short period of days with the described system, can be used to validate a CFD model and/or a hardware design.

Figure 5:
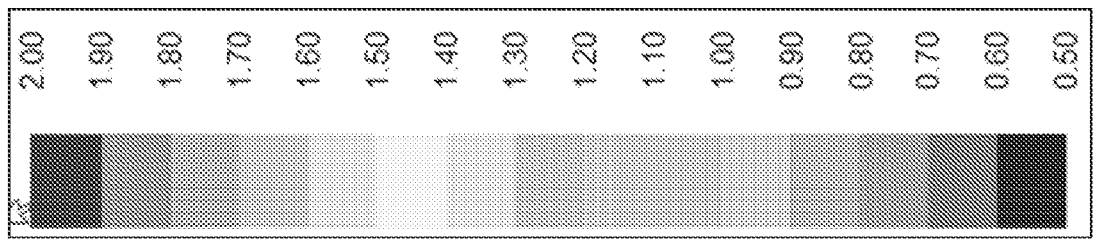
FIGS. 5-12 illustrate an ammonia to $NO_x$ ratio (ANR) distribution for CFD and experimental testing at B50 engine operating conditions.
Figure 5:
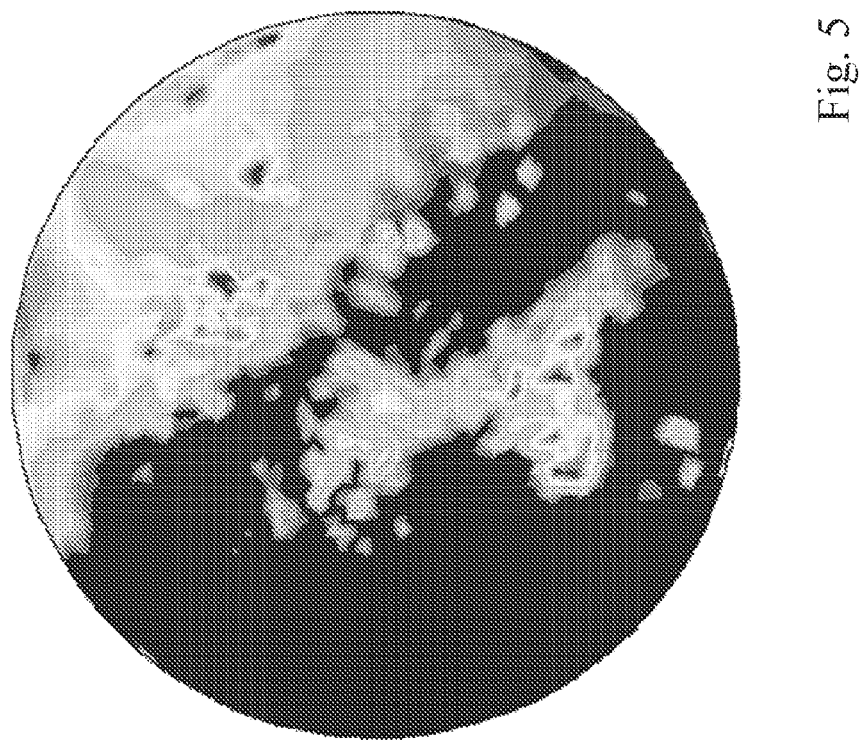
Figure 6:
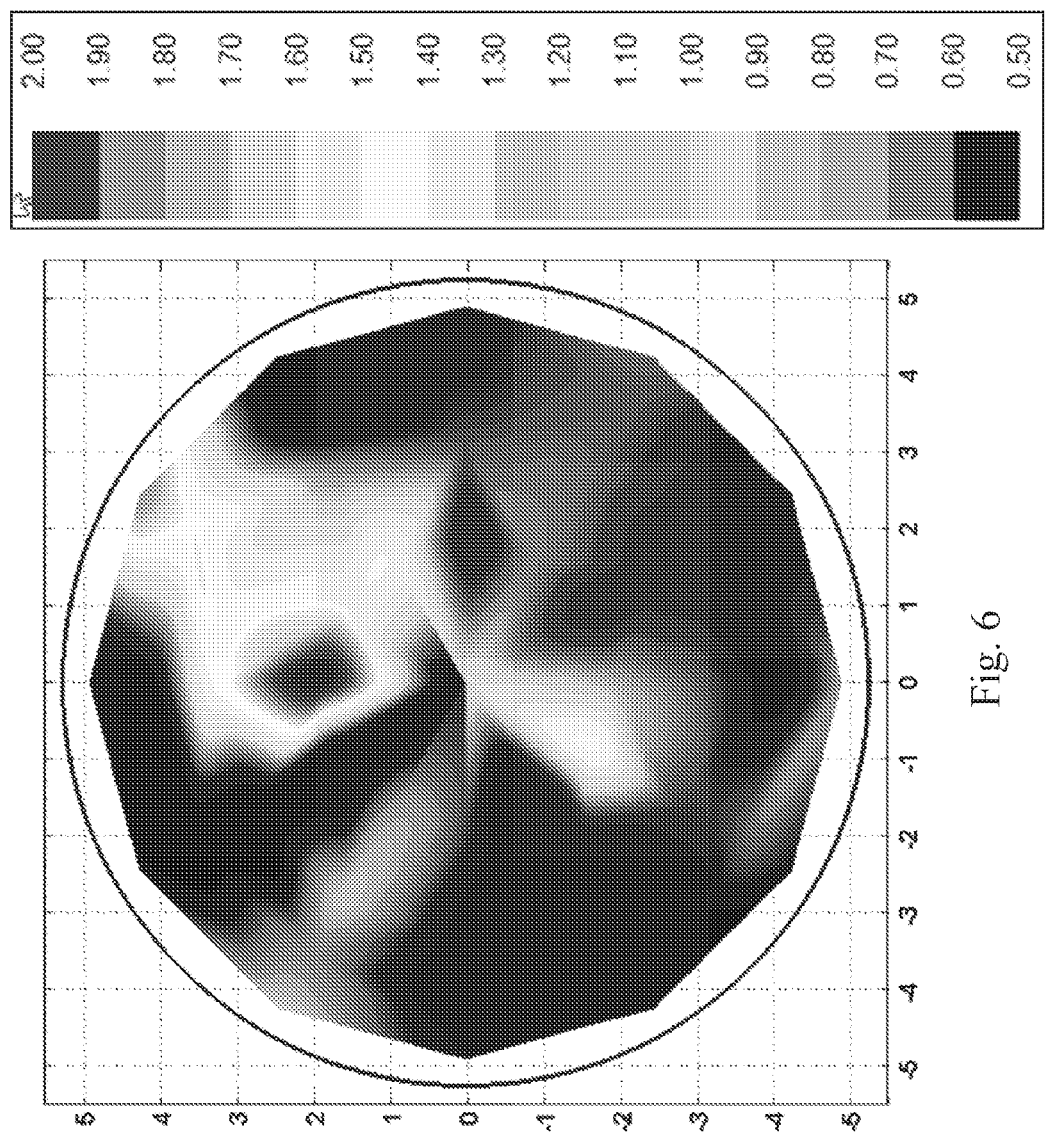
Figure 7:
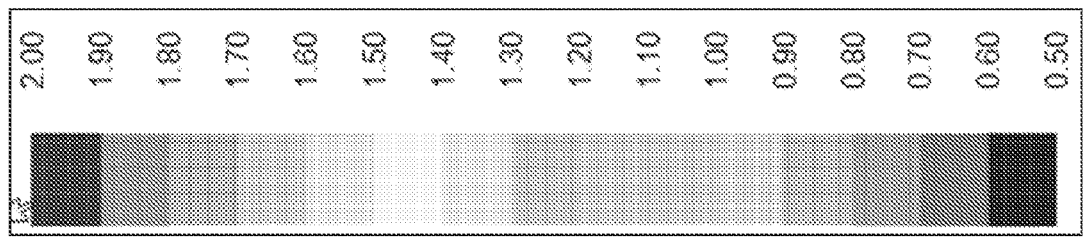
Figure 7:
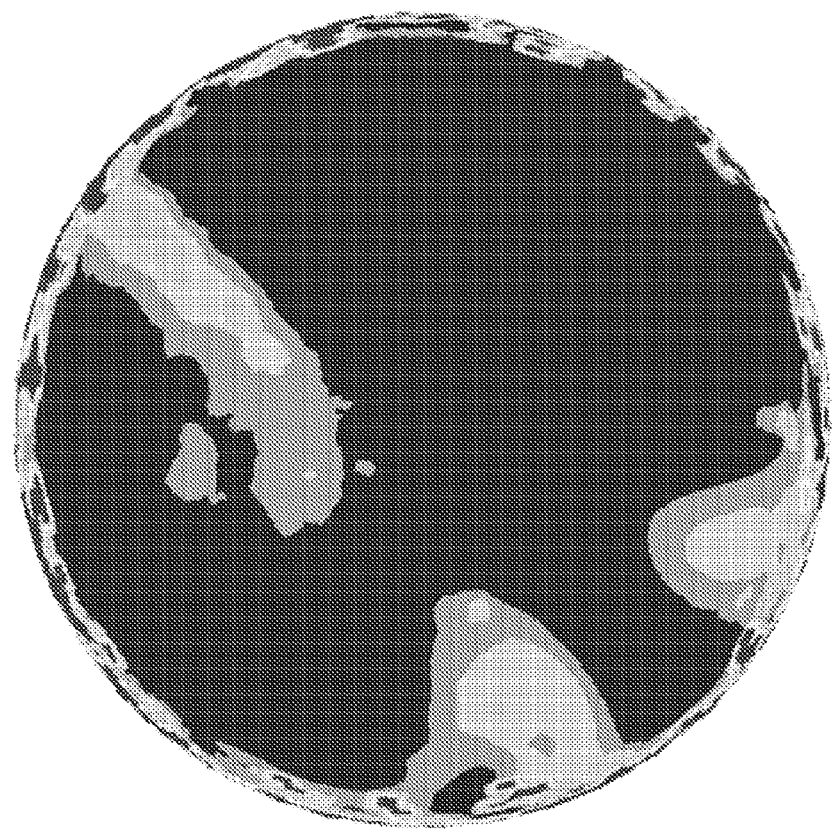
Figure 8:
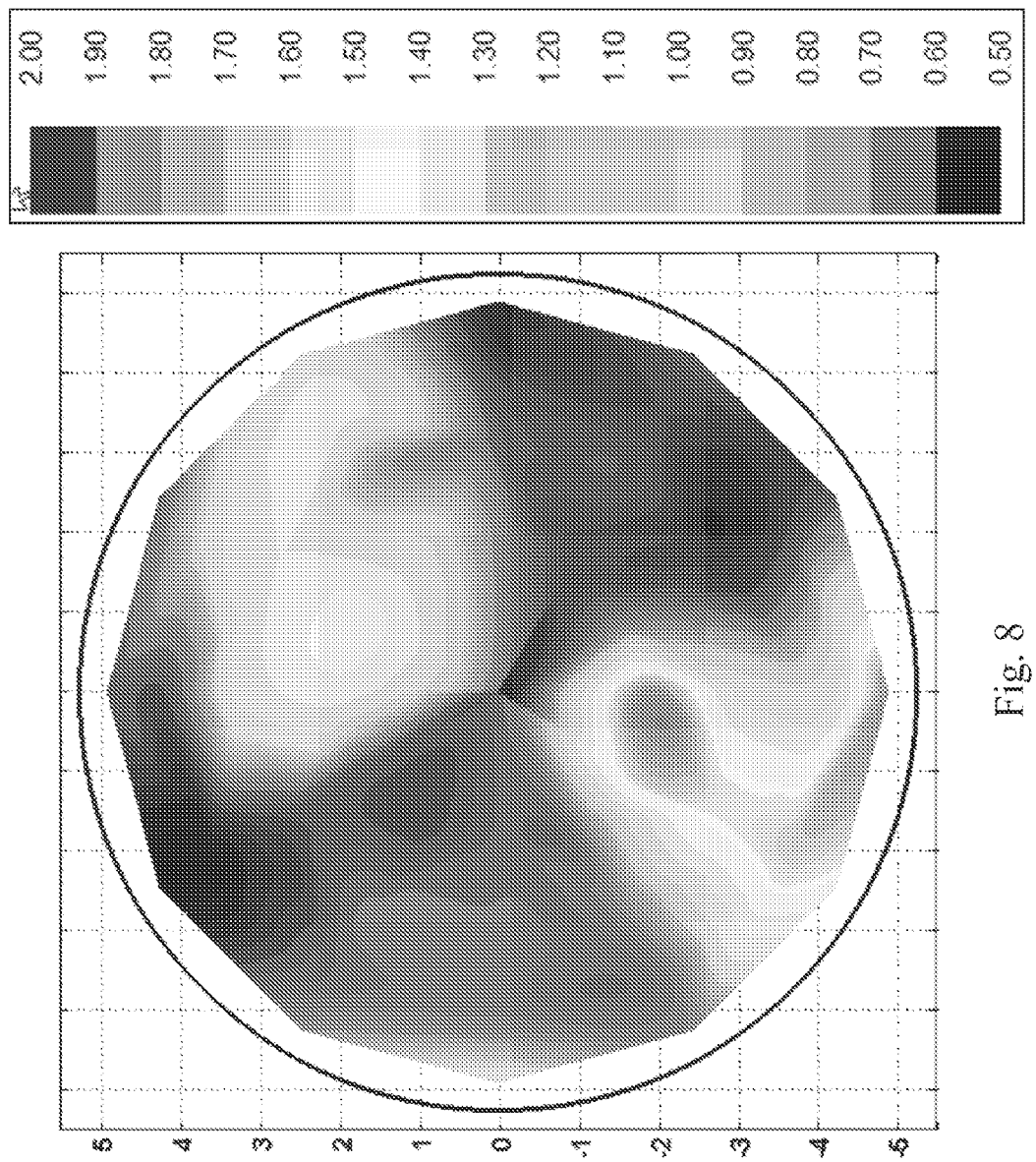
Figure 9:
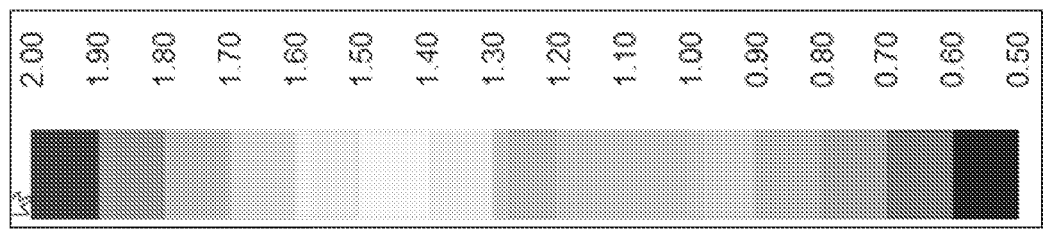
Figure 9:
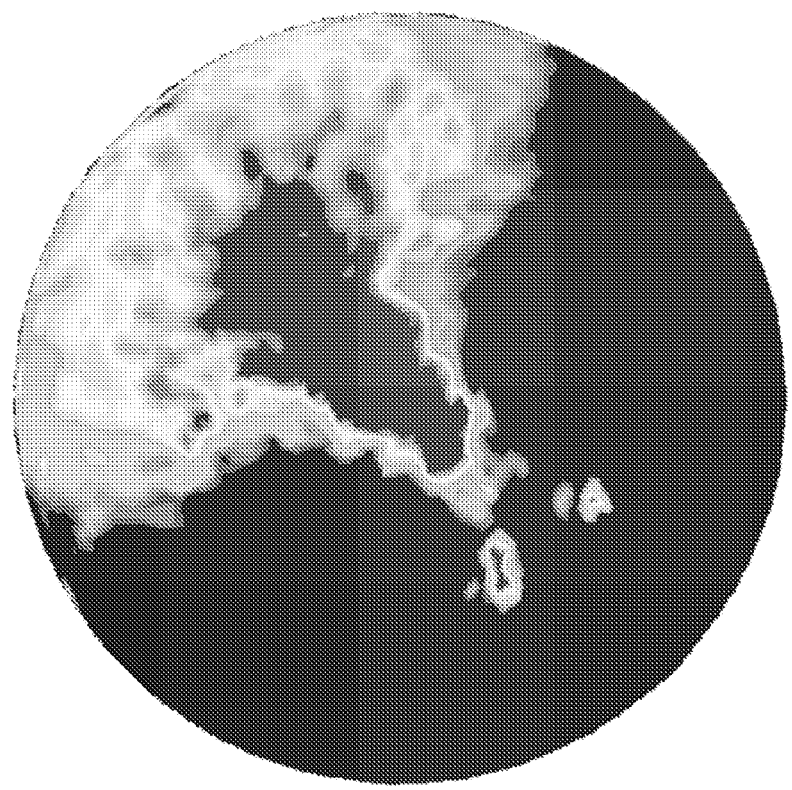
Figure 10:
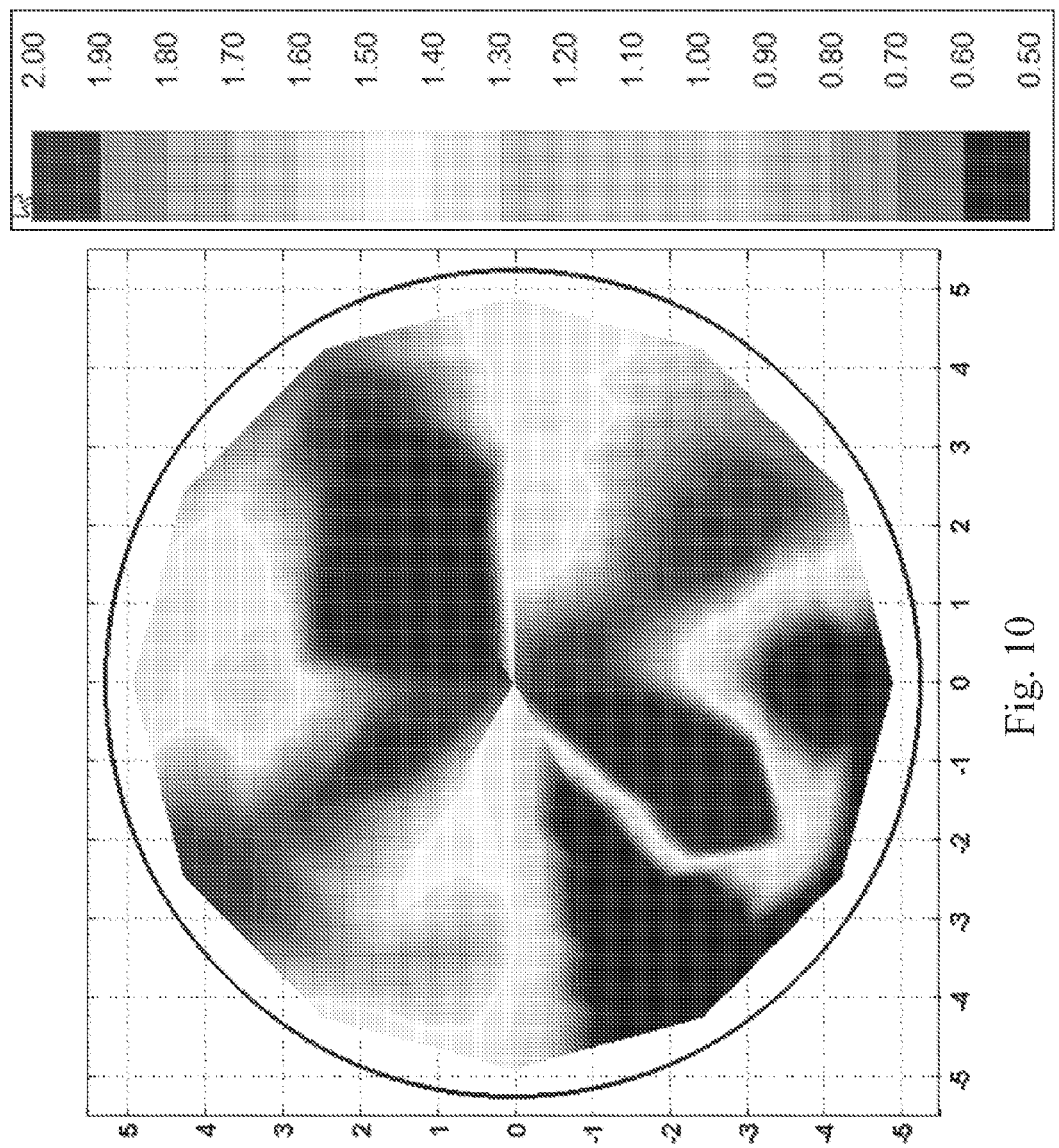
Figure 11:
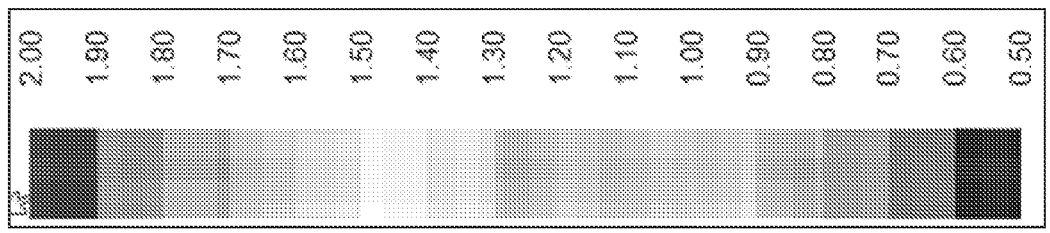
Figure 11:
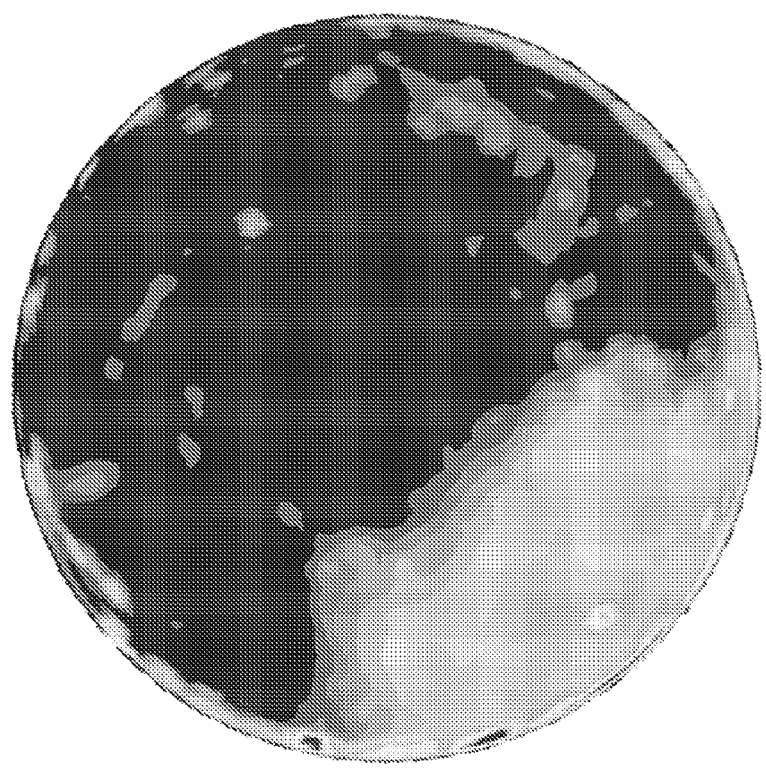
Figure 12:
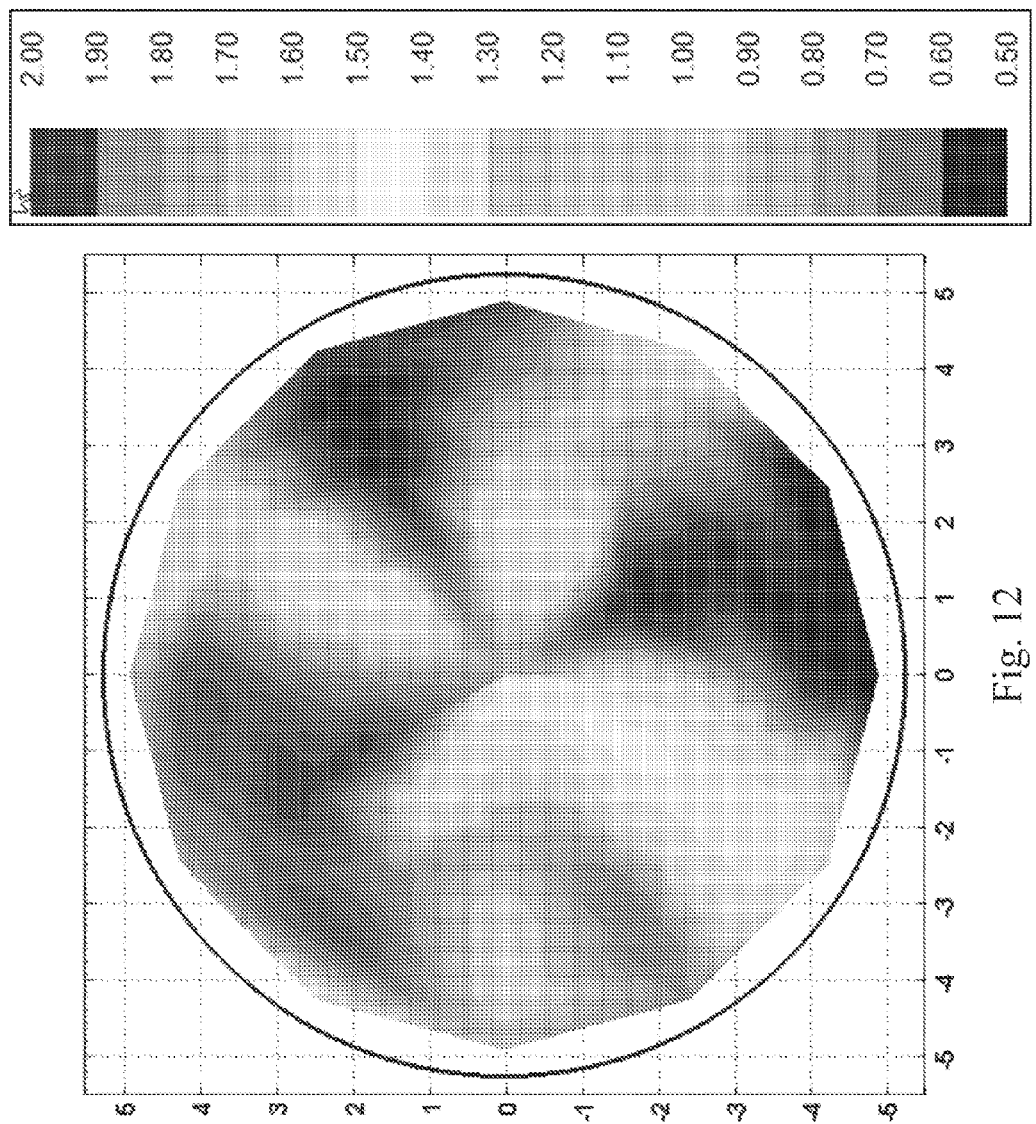

FIGS. 5-12 illustrate experimental test results and CFD calculations for B50 operating conditions. FIG. 5 illustrates a graph of CFD calculation results and FIG. 6 illustrates a graph of experimental test results for an EPA 2010 compliant decomposition tube and SCR end inlet configuration. FIG. 7 illustrates a graph of CFD calculation results and FIG. 8 illustrates a graph of experimental test results for an EPA 2010 compliant decomposition tube and SCR side inlet configuration. FIG. 9 illustrates a graph of CFD calculation results and FIG. 10 illustrates a graph of experimental test results for an EPA 2013 compliant decomposition tube and SCR end inlet configuration. FIG. 11 illustrates a graph of CFD calculation results and FIG. 12 illustrates a graph of experimental test results for an EPA 2013 compliant decomposition tube and SCR side inlet configuration.

Figure 13:
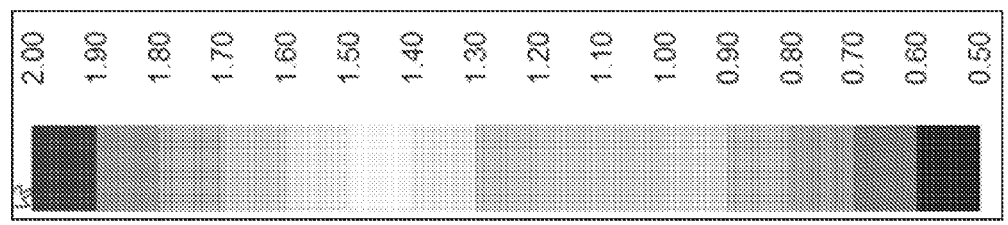
FIGS. 13-22 illustrate an ANR distribution for CFD and experimental testing at C100 engine operating conditions.
Figure 13:
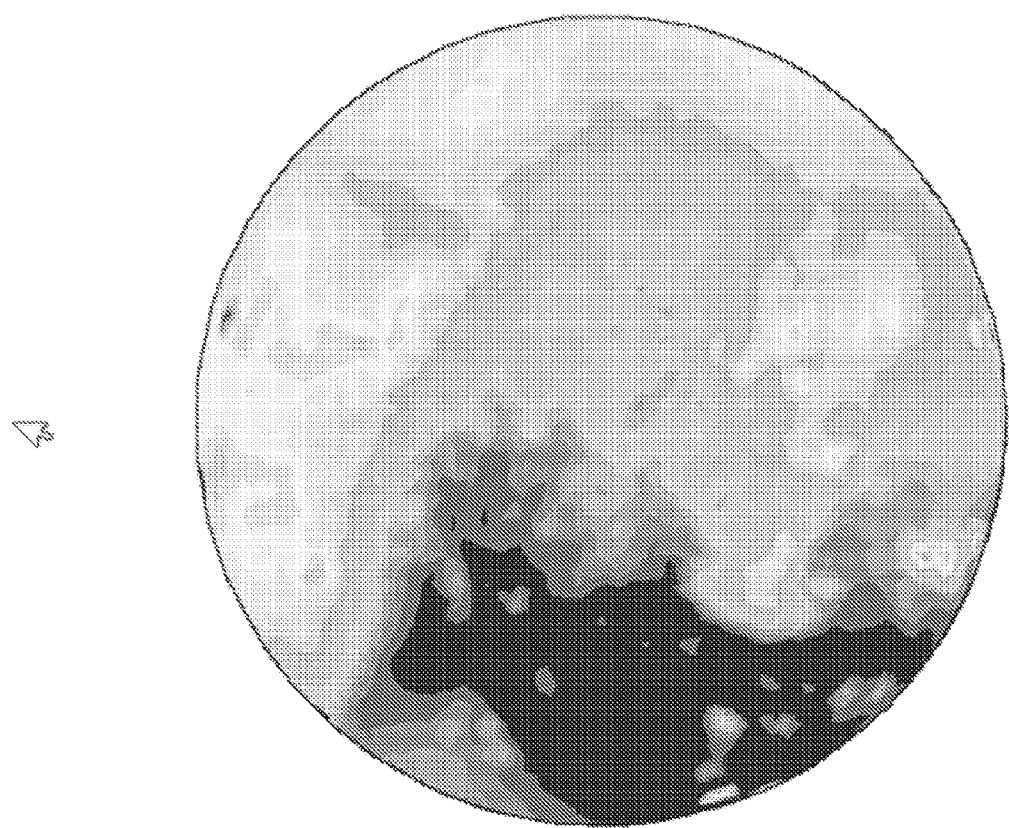
Figure 14:
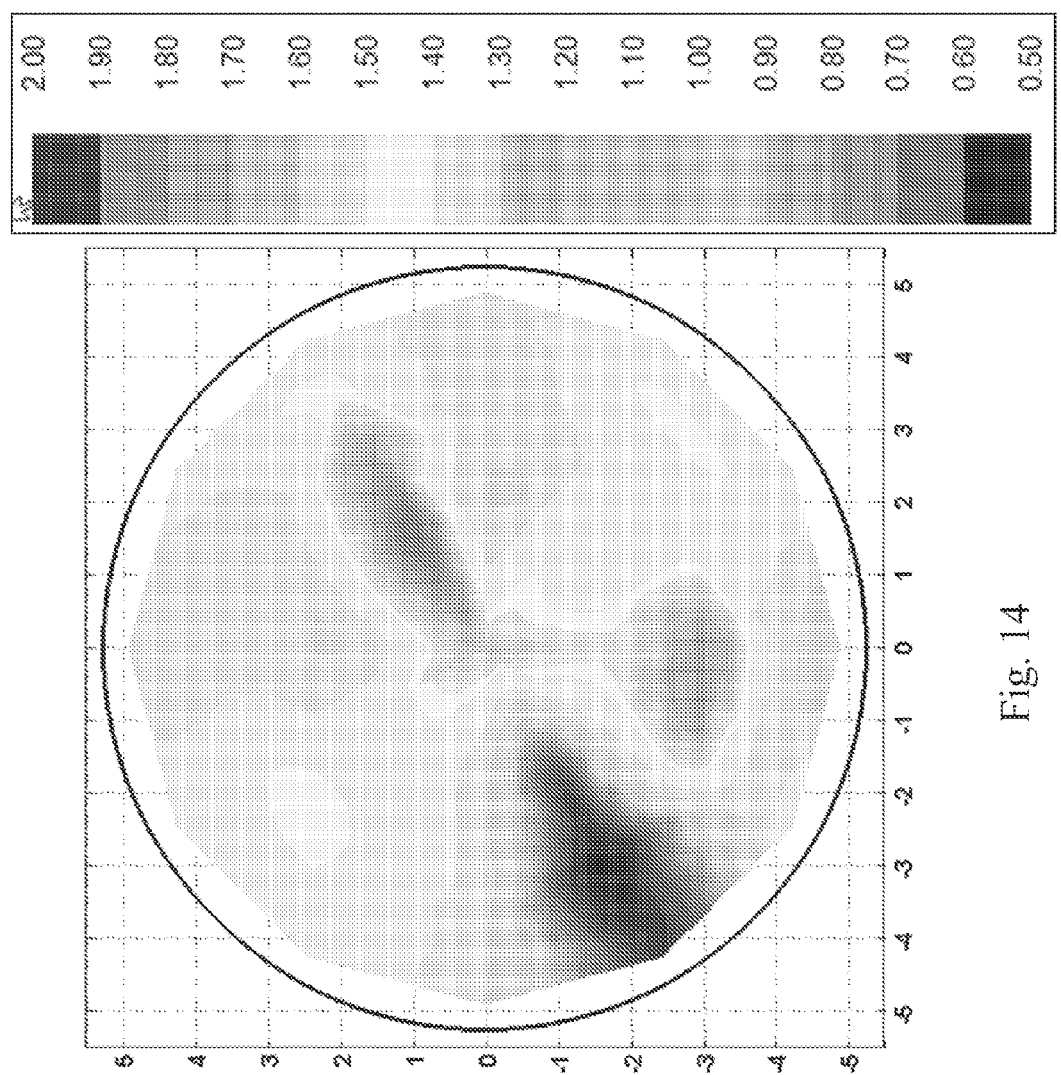
Figure 15:
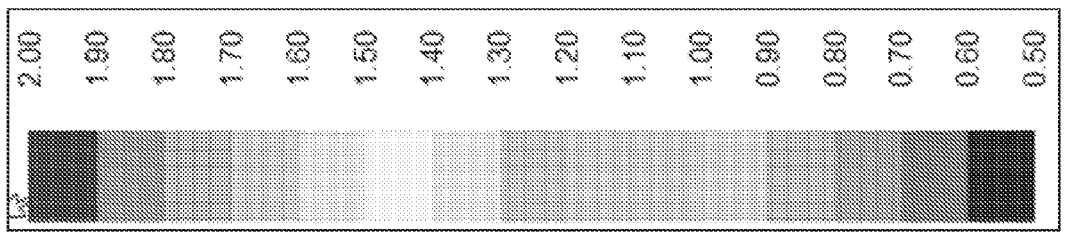
Figure 15:
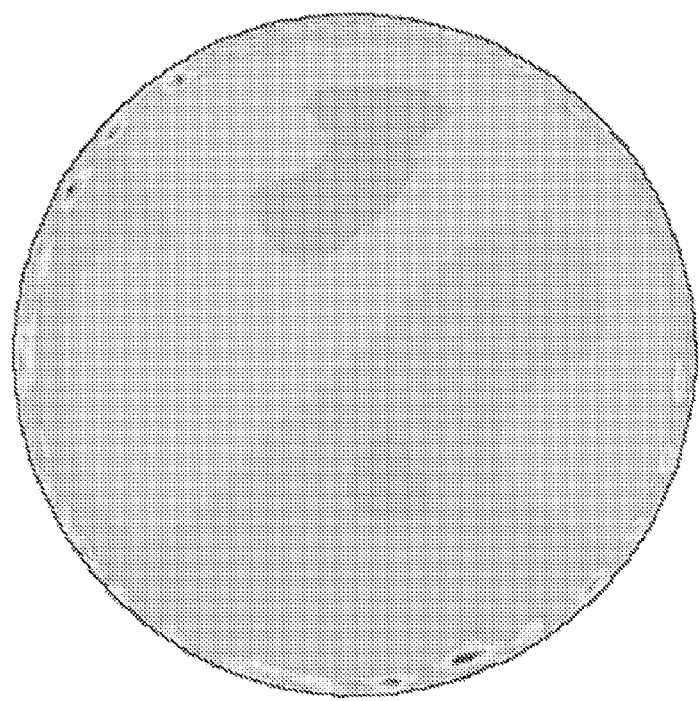
Figure 16:
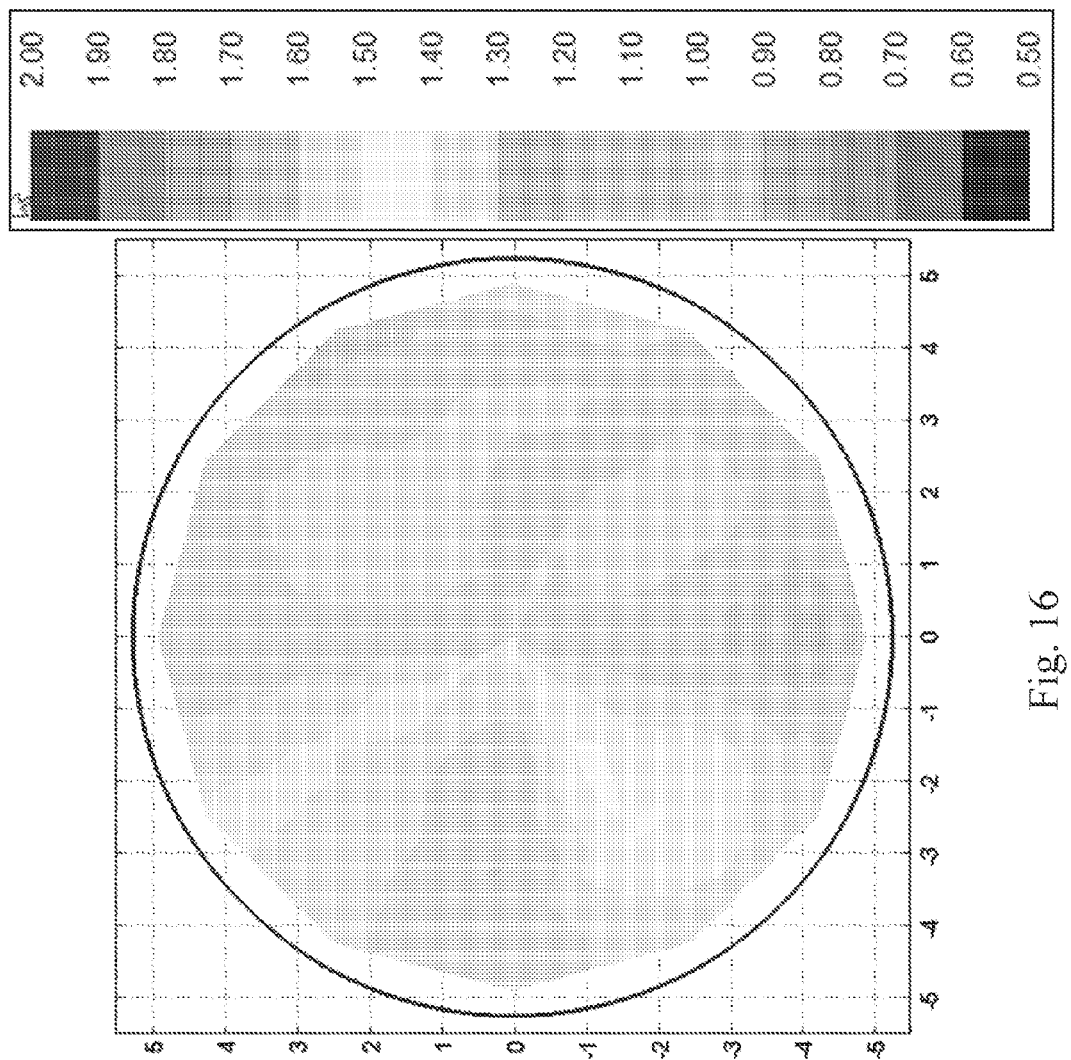
Figure 17:
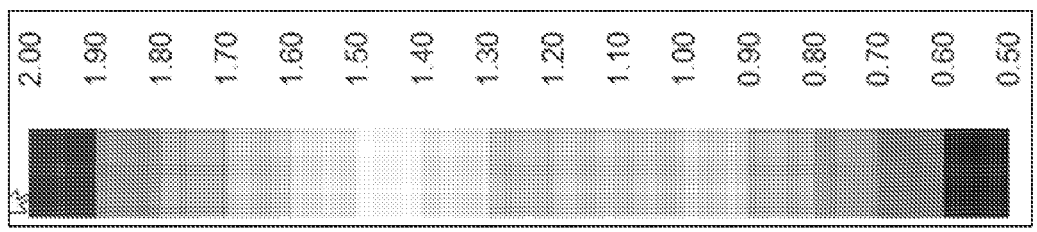
Figure 17:
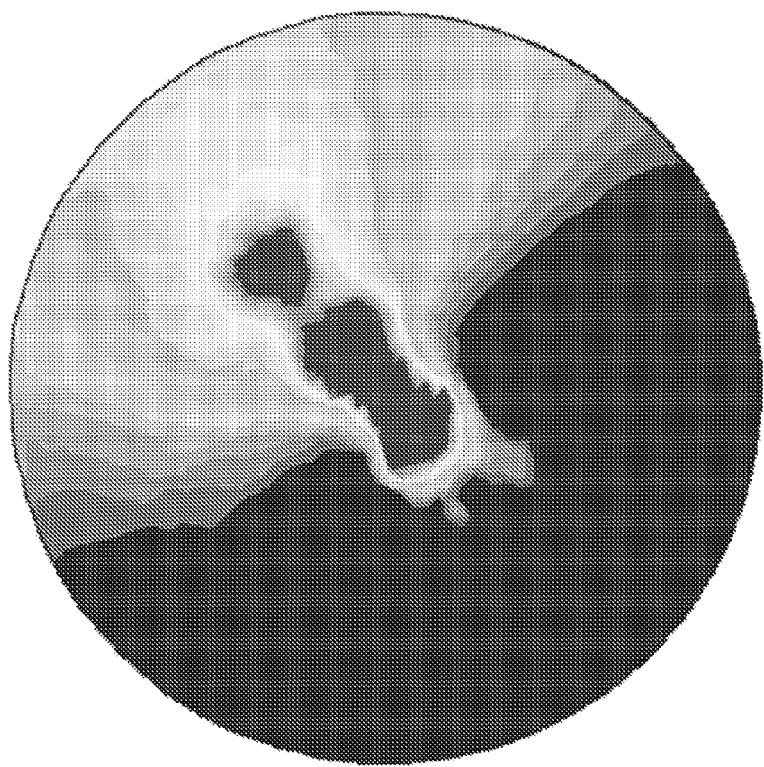
Figure 18:
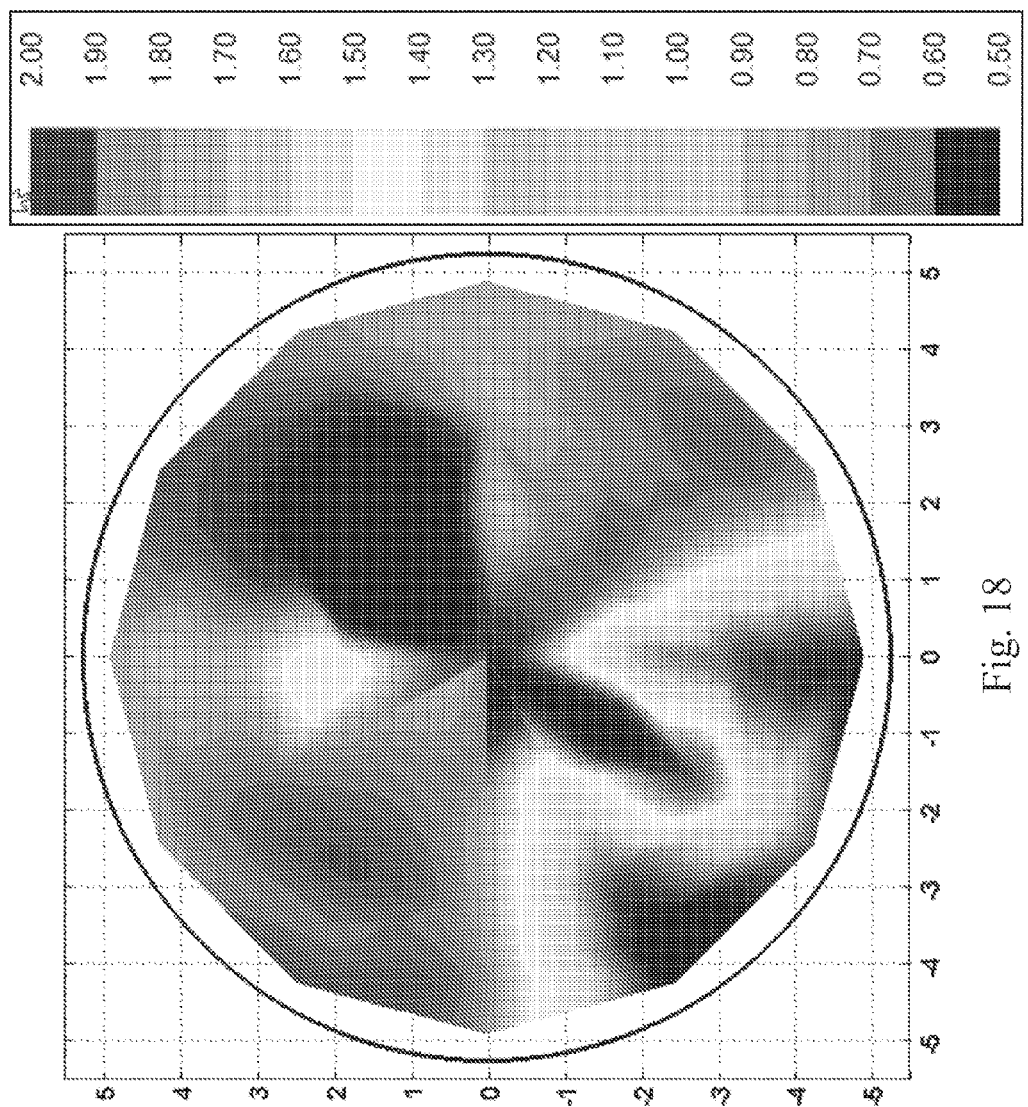
Figure 19:
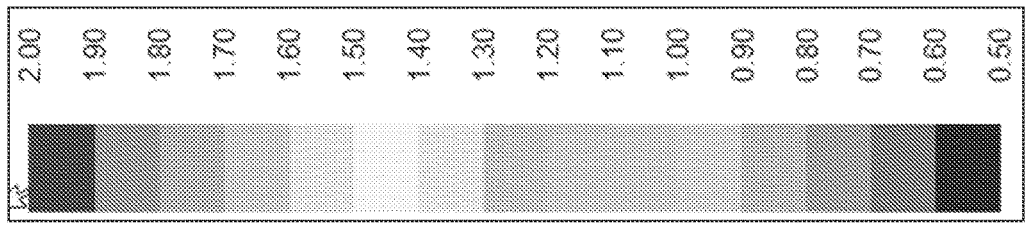
Figure 19:
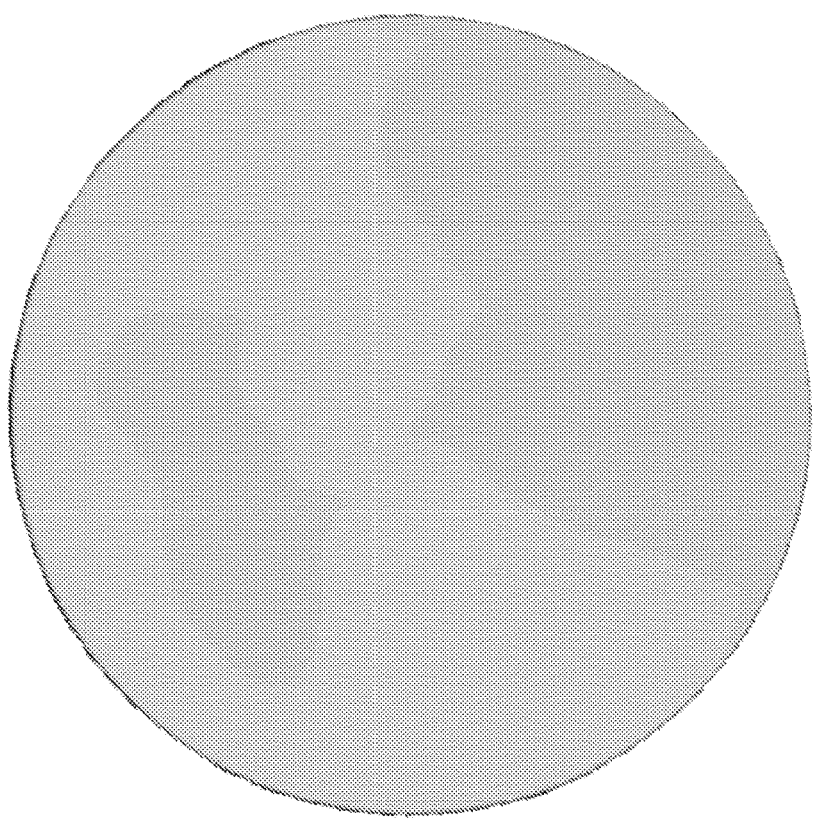
Figure 20:
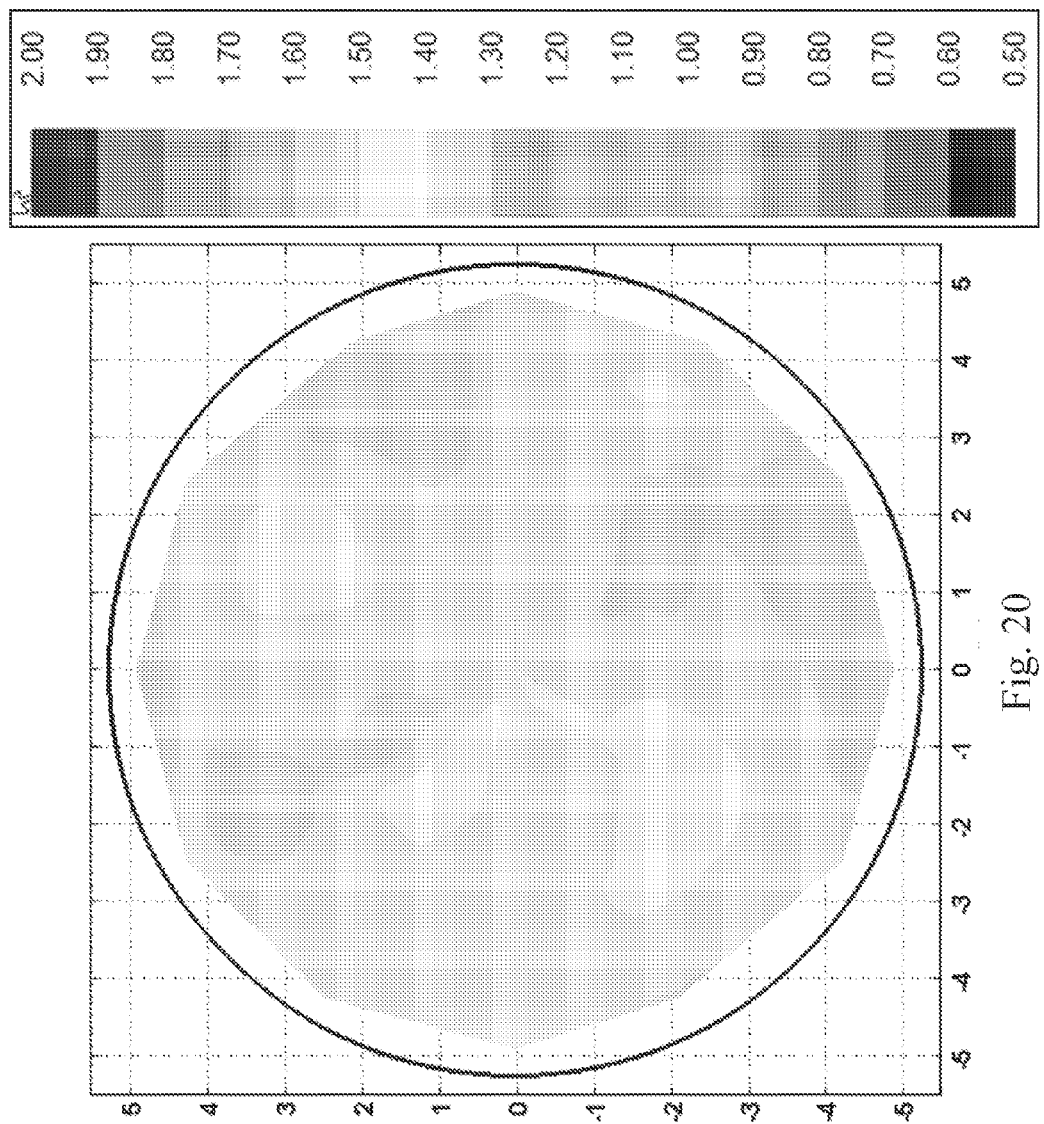
Figure 21:
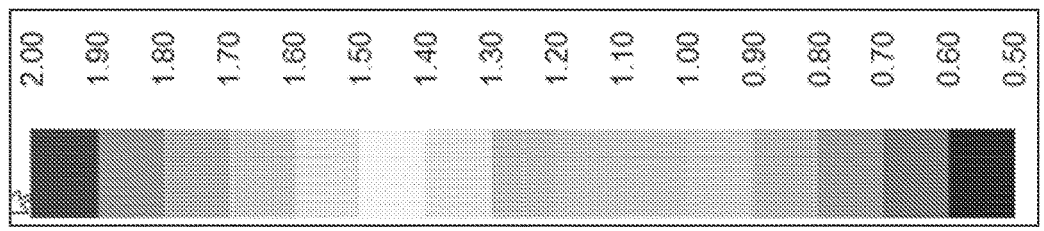
Figure 21:
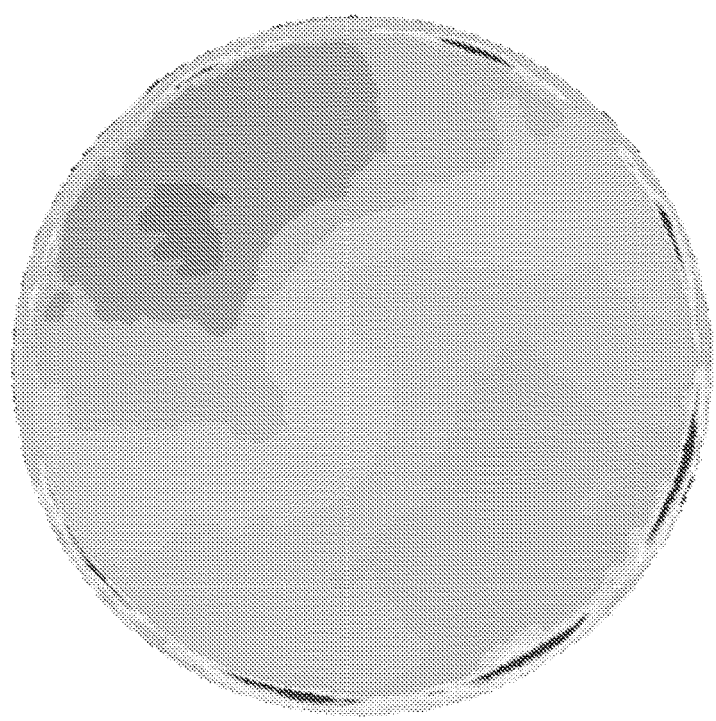
Figure 22:
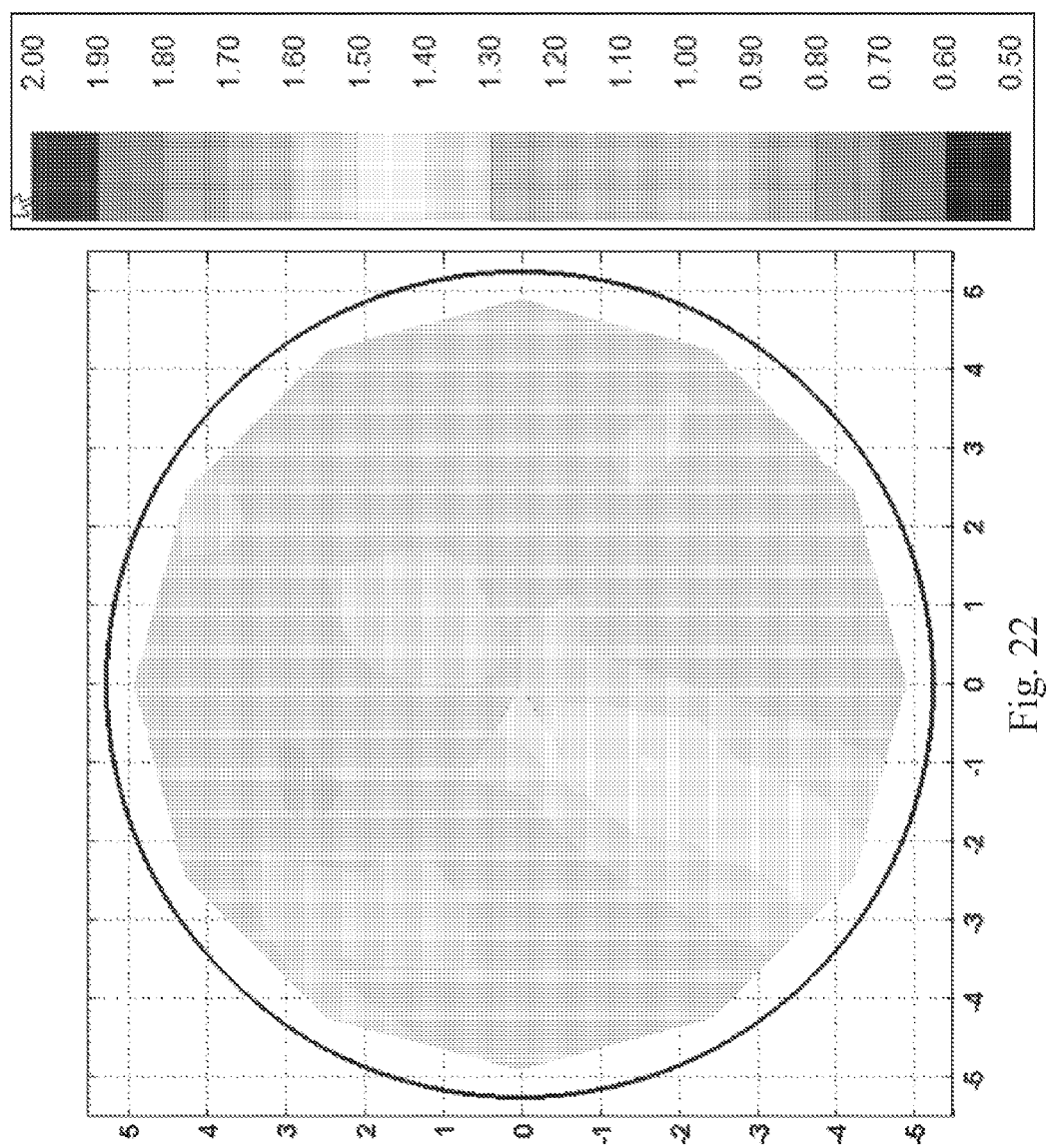

FIGS. 13-22 illustrate comparisons of experimental test results and CFD calculations for C100 operating conditions. FIG. 13 illustrates a graph of CFD calculation results and FIG. 14 illustrates a graph of experimental test results for an EPA 2010 compliant decomposition tube and SCR end inlet configuration. FIG. 15 illustrates a graph of CFD calculation results and FIG. 16 illustrates a graph of experimental test results for an EPA 2010 compliant decomposition tube and SCR side inlet configuration. FIG. 17 illustrates a graph of CFD calculation results and FIG. 18 illustrates a graph of experimental test results for an EPA 2013 compliant decomposition tube and SCR end inlet configuration. FIG. 19 illustrates a graph of CFD calculation results and FIG. 20 illustrates a graph of experimental test results for an EPA 2013 compliant decomposition tube and SCR side inlet configuration. FIG. 21 illustrates a graph of CFD calculation results and FIG. 22 illustrates a graph of experimental test results for an EPA 2013 compliant decomposition tube and SCR end inlet configuration with a cyclone mixer.

It can be observed from FIGS. 5-22 that, for both the B50 and C100 engine operating conditions, the different aftertreatment system configurations, the ANR distribution contours obtained from CFD and from experimental testing are visually similar. Decomposition tube clocking with respect to vertical has significant influence on the ANR distribution across the SCR catalyst face in case of the end inlet configuration. During the experimental testing, the decomposition tube was clocked at 45° in the clockwise direction when viewed from decomp inlet side to outlet. It was ensured that similar orientation was incorporated in the model used for CFD work. Thus, we can see that for the end inlet configuration without cyclone mixer, majority of ANR is concentrated in the top right corner as shown by plots from CFD as well as experimental testing.

For the side inlet configurations, it can be seen from the figures that the ANR distribution across the catalyst face is much more uniform. Presence of elbows in the side inlet configurations causes turbulence and better mixing of $NO_x$ and $NH_3$ resulting in better ANR distribution. As mentioned above, this uniform distribution is captured both in CFD and experimental testing.

Species distribution data shown above was used to calculate the species distribution uniformity indices from both CFD and experimental testing. The details of the CFD, and the specific results of the various hardware configurations tested, are not limiting of the disclosures herein. The system described herein can be utilized to test any CFD and/or hardware configuration.

Equations 2 shown below were used to calculate a uniformity index (UI) from experimental data, and provides one example of how the system can be utilized to provide a UI. The emissions measurement in the downstream at tail pipe out was used for the average value in the denominator in the equation below.

$$\gamma_{LI} = 1 - \frac{1}{2}\left(\sum_{i=1}^{n} \frac{A_i}{A_{tot}} \frac{|v_i - v_{avg}|}{v_{avg}}\right), \text{ where}$$

$$v_{avg} = \left(\sum_{i=1}^{n} \frac{A_i v_i}{A_{tot}}\right)$$

$$A_{tot} = \left(\sum_{i=1}^{n} A_i\right).$$

Equations 2

As mentioned before, since ANR distribution across the SCR catalyst face has significant influence on $NO_x$ conversion performance of the catalyst, ANR UI was calculated using the above mentioned equations and is shown in the subsequent plots.

Figure 23:
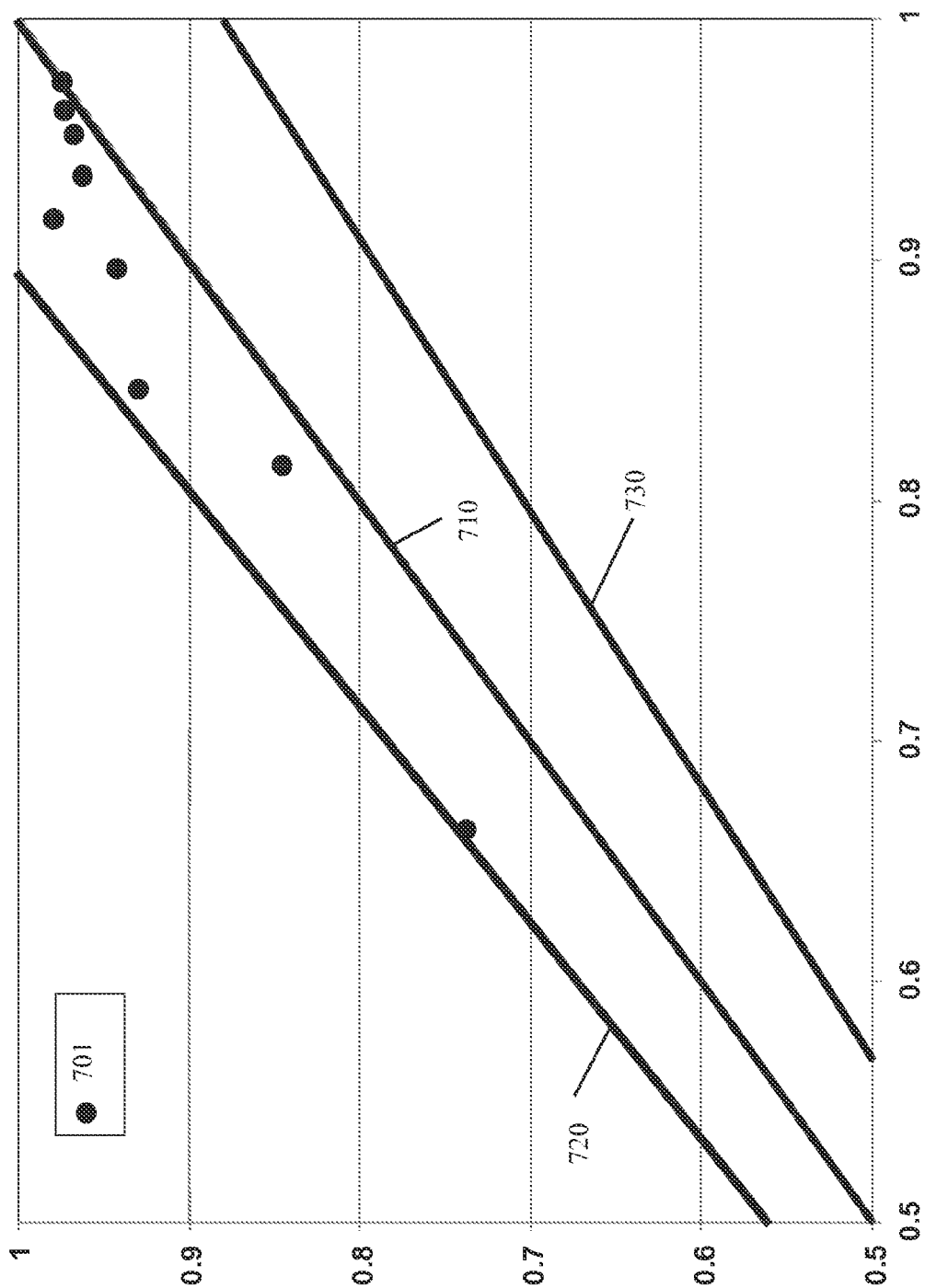
FIG. 23 illustrates a graph of experimental ANR uniformity index (UI) vs CFD predicted UI.

FIG. 23 illustrates ANR UI calculated from experimental measurements plotted against ANR UI predicted from CFD. FIG. 23 illustrates measured ANR UI on its vertical axis and CFD ANR UI on its horizontal axis. FIG. 23 depicts ANR UI points 701, a line of perfect correlation 710, a +12% deviation line 720, and a −12% deviation line 730. Data of the type shown in FIG. 23 can be utilized to quantify the quality of a CFD model. It can be observed that the measured ANR UI is greater than the CFD predicted UI for all the points. This is because localized higher concentration patches observed at the periphery in the distribution plots from CFD cause a drop in UI value. The experimental hardware was not utilized to measure close to the periphery of the catalyst. The maximum error between the measured ANR UI and CFD predicted ANR UI was calculated and is shown in the figure with black lines. The measured ANR UI is within ±12% agreement with the CFD predicted ANR UI. In the example, the 12% error band is acceptable considering the differences between the CFD analysis and experimental testing which are outlined below. One of skill in the art will understand an acceptable error band for a given application having the benefit of the disclosures herein.

Some differences between the CFD analysis and the experimental testing in the example having data depicted in FIG. 23 include:

(1) Experimental data was collected after five minutes of running at a particular grid location. This was the time required for the conditions and emissions to stabilize before data could be sampled. The total run time for the test for one configuration was forty eight hours. On the contrary CFD simulation data was obtained from one injection pulse which was for duration of one second.

(2) Experimentally measured UI was calculated from emissions measurements at forty eight points. The CFD model contains a mesh of approximately 4000 cells and data from all of them is used to calculate the CFD predicted UI.

(3) Emissions measurement was not performed in the experimental setup within the peripheral area (~16.5%) of the catalyst and hence was not used in calculation of experimentally measured UI. CFD predicted UI calculation throughout the entire area of the catalyst face.

Figure 24:
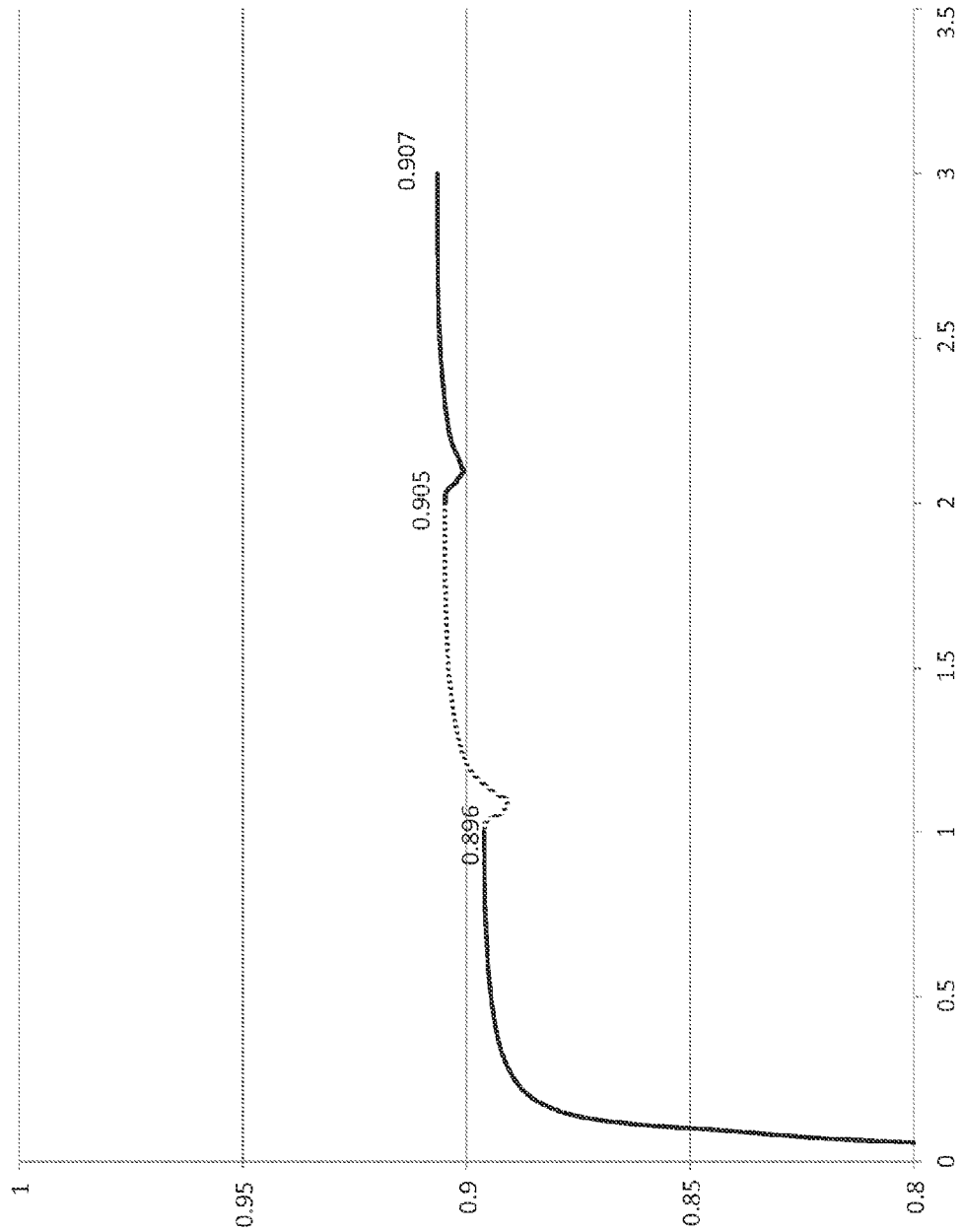
FIG. 24 is a graph illustrating an exemplary effect of multiple injection pulses on CFD predicted ANR UI.

To understand the effect of the first difference, multiple injections pulses were simulated for one of the configurations and CFD predicted UI was calculated from the same and is shown in the graph of FIG. 24 which illustrates an ANR index on its vertical axis and time in seconds on its horizontal axis. It can be observed that there is a slight increase in UI when multiple injection pulses are simulated. Extent of change will be dependent on configuration and test conditions. The change will be small when the percentage evaporation of urea is high.

Figure 25:
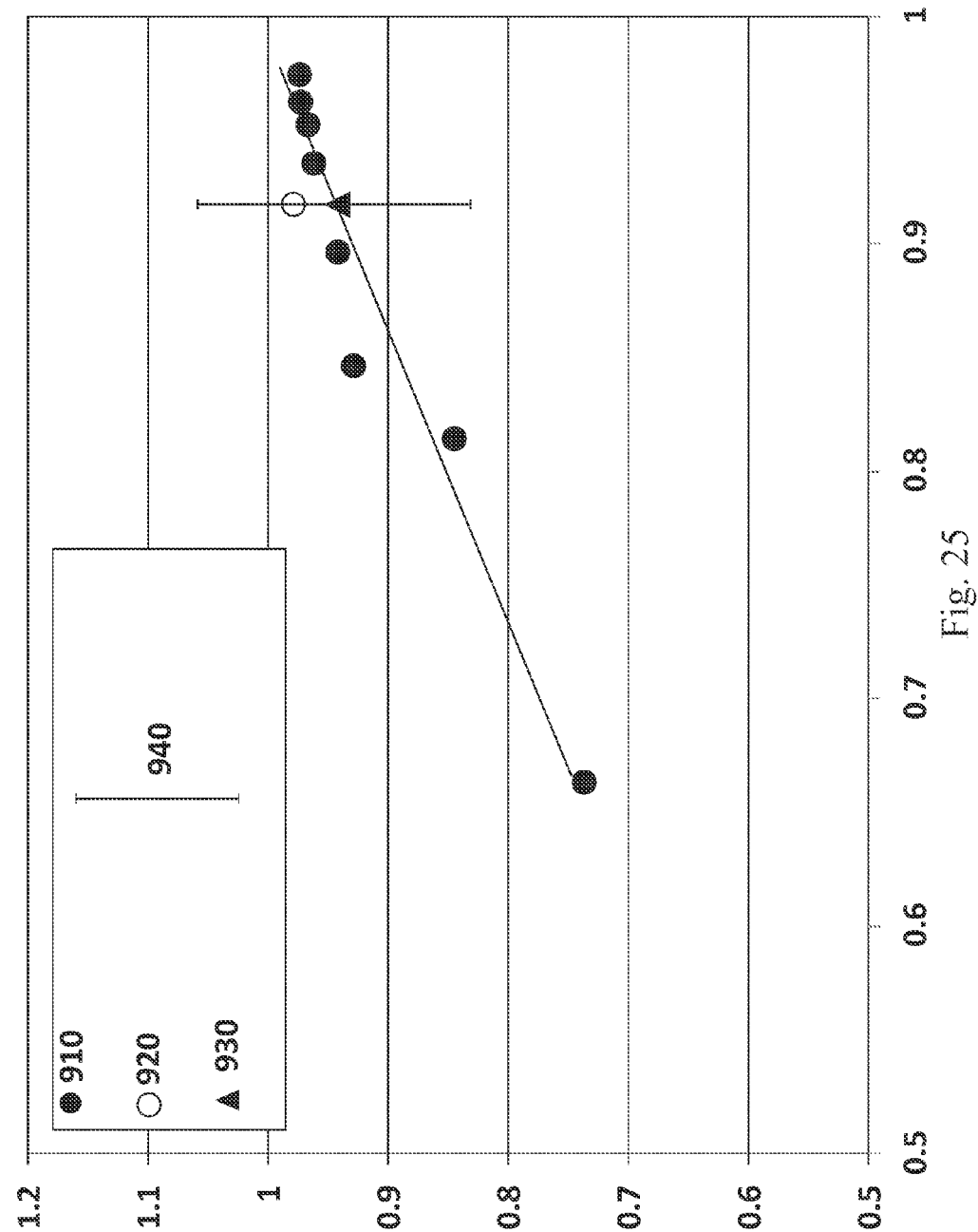
FIG. 25 is a graph illustrating an exemplary correlation between measured ANR UI and CFD predicted ANR UI.

In the test operations, data from eight of the nine data points collected from the different configurations were used to develop a correlation between experimentally measured ANR UI and CFD predicted ANR UI. The data point from the EPA 2013 end inlet configuration with cyclone mixer was used to validate the correlation. The corresponding plot is shown in FIG. 25. The results of the particular correlation test are not important, but it can be seen that the system can be used to generate data such as that depicted in FIG. 25 to calibrate or verify a CFD model for the system.

Measured ANR UI calculated from the equation is plotted along with the experimentally measured ANR UI for the EPA 2013 end inlet with cyclone mixer configuration. The graph of FIG. 25 illustrates measured ANR UI on its vertical axis and CFD predicted ANR UI on its horizontal axis. Points 910 are eight ANR UI measurement points. Point 920 is a measured ANR UI for an EPA 2013 compliant SCR end inlet configuration with a cyclone mixer at C100 engine operating conditions. Point 930 is an equation predicted ANR UI for an EPA 2013 compliant SCR end inlet configuration with a cyclone mixer at C100 engine operating conditions. The correlation equation of the line illustrated in FIG. 25 is y=0.7808x+0.2298 and $R^2$=0.9484. FIG. 25 also illustrates an error bar 940 encapsulating the ±12% error shown in FIG. 23 and it can be observed that the experimentally measured ANR UI falls within the errors bars. Thus, it can be concluded that the equation is valid for the purposes of the system tested in FIG. 25. The error bar 940 and determinations of validity are selectable according to the needs of the user for a particular system.

A number of exemplary embodiments will now be further described. One exemplary embodiment includes a sampling disk comprising an outer housing comprising a diameter of a target aftertreatment system component, a sampling probe having a sampling tip and an extension, wherein the extension is at least one-half diameter of the outer housing, and two linear actuators operationally coupled to the extension and structured to position the sampling tip at any cross-sectional position within the outer housing. The present exemplary embodiment may include one or more the following features. The extension may sealably pass through the outer housing. The outer housing may be rotatable. Rotation of the outer housing may change an angle of linear actuation of the extension in response to the linear actuators, and the angle change may be relative to an aftertreatment component. The aftertreatment component comprises at least one component selected from the components consisting of: an oxidation catalyst, a particulate filter, a catalyzed particulate filter, a decomposition tube, a hydrolysis catalyst, a selective reduction catalyst, a turbocharger outlet, and a portion of an exhaust pipe.

Another exemplary embodiment is a method utilizing a system according to the preceding exemplary embodiment. The method includes determining at least one exhaust gas composition constituent at a plurality of cross-sectional points to determine a distribution of the exhaust gas composition constituent. The present exemplary embodiment may include one or more the following features. The method may include determining the plurality of cross-sectional points in response to an equal area method. The method may include determining at a number of the plurality of cross-sectional points within a single day, the number comprising a number greater than five, greater than ten, greater than twenty-five, and/or greater than forty. The method may include performing the determining at a plurality of engine operating conditions. The plurality of engine operating conditions may include a B50 point and a C100 point. The method may include verifying a CFD model in response to the determining. The method may include verifying a hardware design in response to the determining and/or the verifying. The exhaust gas composition constituent may include a constituent that can be correlated to a reductant distribution. The exhaust gas composition constituent may comprise a constituent that can be correlated to a localized reductant:$NO_x$ ratio.

A further exemplary embodiment is an exhaust testing apparatus. The apparatus includes a housing defining an exhaust flow path extending from a housing inlet to a housing outlet, the housing inlet and the housing outlet configured to connect with respective first and second portions of an exhaust aftertreatment system, at least a portion of the housing being selectably rotatable relative to at least one of the first and second portions of the exhaust aftertreatment system. The apparatus further includes an arm extending from the housing into the exhaust flow path, an exhaust probe coupled with the arm and positioned at a location in the exhaust flow path, the exhaust probe configured to measure an exhaust constituent, and an actuator configured to extend and retract the arm to vary the location of the exhaust probe in the exhaust flow path. The exhaust probe is moveable to a plurality of locations within a portion of a sectional area of the exhaust flow path through a combination of rotation of the housing and extension and retraction of the arm. The present exemplary embodiment may further include the exhaust aftertreatment system which may include a first aftertreatment component positioned upstream from the housing inlet, a second aftertreatment component positioned downstream from the housing outlet, and an injector positioned upstream from the first aftertreatment component. The first aftertreatment component may be a hydrolysis catalyst, the second aftertreatment component may be an SCR brick, and the injector may be coupled with a supply of aqueous urea solution. In certain forms the probe comprises an FTIR probe configured to measure exhaust species concentration. In certain forms the sectional area comprises about 50% or more of the total sectional area of the exhaust flow path. In certain forms the plurality of positions comprise substantially all positions within the sectional area. In certain forms the apparatus further includes a second arm extending from the housing into the exhaust flow path, a second exhaust probe coupled with the second arm and positioned at a second location in the exhaust flow path, the second exhaust probe configured to measure exhaust species concentration, and a second actuator configured to extend and retract the second arm effective to vary the location of the second exhaust probe within the exhaust flow path. The second exhaust probe is moveable to a second plurality of locations within a second portion of a second sectional area of the exhaust flow path through a combination of rotation of the housing and extension and retraction of the second arm. In certain forms the sectional area and the second sectional area each comprises about 50% the total sectional area of the exhaust flow path.

Another exemplary embodiment is a system including an exhaust aftertreatment system configured to receive exhaust from an internal combustion engine and a test device operatively coupled with the exhaust aftertreatment system, the test device including an exhaust passage configured to receive exhaust from the exhaust aftertreatment system, an extension member extending into the exhaust passage, a probe coupled with the extension member and configured to measure a constituent of the exhaust, and an actuator configured to move the extension member. The system is configurable to position the probe in a plurality of locations in the exhaust passage through movement of the extension member without interrupting exhaust flow in the exhaust passage. In certain forms the test device further includes a second extension member extending into the exhaust passage, a second probe coupled with the second extension member and configured to measure a constituent of the exhaust, and a second actuator configured to move the second extension member, wherein the system is configurable to position the second probe in a second plurality of locations in the exhaust passage through movement of the second extension member without interrupting exhaust flow in the exhaust passage. In certain forms the plurality of locations of the probe intersect a line extending through a center point of the exhaust passage and the second plurality of locations of the second probe intersect a second line extending through the center point. In certain forms the system is configurable to measure a constituent of the exhaust with one of the first probe and the second probe at substantially any location in a sectional area of the exhaust passage through a combination of linear movement of the extension member, linear movement of the second extension member, and rotation of the extension member and the second extension member relative to the exhaust flow passage. In certain forms the linear movement and the rotation of the extension member are effective to position the first probe in substantially any position in a first 50% of the sectional area of the exhaust passage and the linear movement and the rotation of the second extension member are effective to position the second probe in substantially any position in a second 50% of the sectional area of the exhaust passage. In certain forms the extension member and the second extension member are rotatable by at least 90 degrees relative to the exhaust aftertreatment system.

It shall be appreciated that the number and spacing of positions that comprise substantially all positions within a given sectional area depend upon system-specific parameters that would be appreciated by one of skill in the art contemplating a specific system. One example of substantially all positions includes spacing of the positions such that a gradient of interest is lower than a threshold value between any adjacent positions, where the gradient may be a composition, temperature, flow rate, and/or material phase (e.g. vapor versus liquid phase) difference. Another example of substantially all positions includes spacing of the positions such that each measurement position covers less than a threshold cross-section of the overall flow area, which threshold cross-section includes a selected value depending upon the application, and which may include not greater than 1 cm$^2$, not greater than 5 cm$^2$, not greater than 10 cm$^2$, and/or not greater than 25 cm$^2$, but may include other area values. Yet another example of substantially all measurements includes sufficient coverage of measurements such that uncovered areas are either too small to be of concern, or that are not of concern for other reasons—for example where face plugging on a catalyst is known to occur within a certain region on the catalyst, an area where face plugging is not a concern may not be covered by a measurement and yet substantially all positions within a sectional area may be measured.

It shall be appreciated that a measurement covering a position indicates that the measurement is a measurement within a given area that is in a position expected to be descriptive of a given area. Intentional measurement redundancy, for example, may provide for multiple measurements within a given area, where a measurement nevertheless covers that area. The area covered by the measurements may be the same or distinct between measurements. It shall be further appreciated that, depending upon the specific system being contemplated, the information relevant to determining substantially all positions may include the cell density of a component, the flow rates in the measurement area, the temperatures and/or heat transfer environment in the measurement area, the expected issues in the system due to non-uniformity of aftertreatment flow, the catalyst loading and distribution geometry of catalyst within a component, the gradients expected in a system, and/or the gradients that are acceptable in the system. It shall be appreciated that one of skill in the art, having information relevant to a particular system, and having the benefit of the disclosures herein, can readily determine a plurality of positions that comprise substantially all positions within the sectional area.

An additional exemplary embodiment is a method including connecting a test device to an exhaust aftertreatment system, the test device comprising an exhaust flow path, a support extending into the exhaust flow path, a probe coupled with the support, and an actuator configured to move the support. The method further includes operating an engine to output exhaust to the exhaust aftertreatment system, performing a first exhaust measurement with the probe in a first location in the exhaust flow path, operating the actuator to move the probe to a second location in the exhaust flow path, performing a second exhaust measurement with the probe in the second location, rotating at least a portion of the test device to move the probe to a third location in the exhaust flow path, and performing a third exhaust measurement with the probe in the third location. In certain forms the method further includes determining a distribution of at least one exhaust gas constituent based at least in part upon the first exhaust measurement, the second exhaust measurement, and the third exhaust measurement. In certain forms the method further includes repeating said operating the actuator and said rotating at least a portion of the test device a plurality of times effective to position the probe at a plurality of locations within a portion of a sectional area of the exhaust flow path in addition to the first location, the second location, and the third location, and performing a plurality of measurements of exhaust species concentration with the probe in each of the plurality of locations. In certain forms the plurality of locations are selected based upon an equal area method. In certain forms the method further includes correlating the distribution of the exhaust gas composition constituent to at least one of a reductant distribution and a localized ratio of reductant to NO$_x$. In certain forms the method further includes verifying a CFD model based upon the determining. In certain forms the method further includes verifying a hardware design in response to at least one of the determining and the verifying.

While the invention has been illustrated and described in detail in the drawings and foregoing description, the same is to be considered as illustrative and not restrictive in character, it being understood that only certain exemplary embodiments have been shown and described. Those skilled in the art will appreciate that many modifications are possible in the example embodiments without materially departing from this invention. Accordingly, all such modifications are intended to be included within the scope of this disclosure as defined in the following claims.

In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. An exhaust testing apparatus, the apparatus comprising:
a housing defining an exhaust flow path extending from a housing inlet to a housing outlet, the housing inlet and the housing outlet configured to connect with respective first and second portions of an exhaust aftertreatment system, at least a portion of the housing being selectably rotatable relative to at least one of the first and second portions of the exhaust aftertreatment system;
a first arm extending from the housing into the exhaust flow path;
a second arm extending from the housing into the exhaust flow path;
a first exhaust probe coupled with the first arm and positioned at a location in the exhaust flow path, the first exhaust probe configured to measure an exhaust species concentration;
a second exhaust probe coupled with the second arm and positioned at a second location in the exhaust flow path, the second exhaust probe configured to measure the exhaust species concentration;
a first actuator configured to extend and retract the first arm to vary the location of the exhaust probe in the exhaust flow path, wherein the first arm is moveable between (i) a first retracted position, in which the first exhaust probe is located adjacent to an inner surface of the housing, and (ii) a first extended position, in which the first exhaust probe is located at a position beyond a central axis of the housing; and
a second actuator configured to extend and retract the second arm to vary the location of the second exhaust probe in the exhaust flow path, wherein the second arm is moveable between (i) a second retracted position, in which the second exhaust probe is located adjacent to the inner surface of the housing, and (ii) a second extended position, in which the second exhaust probe is located at the position beyond the central axis of the housing;
wherein the first exhaust probe is moveable to a first plurality of locations within a first portion of a sectional area of the exhaust flow path through a combination of rotation of the housing and extension and retraction of the first arm; and
wherein the second exhaust probe is moveable to a second plurality of locations within a second portion of the sectional area of the exhaust flow path through a combination of rotation of the housing and extension and retraction of the second arm.

2. The apparatus of claim 1 further comprising the exhaust aftertreatment system, wherein the exhaust aftertreatment system includes a first aftertreatment component positioned upstream from the housing inlet, a second aftertreatment component positioned downstream from the housing outlet, and an injector positioned upstream from the first aftertreatment component.

3. The apparatus of claim 2 wherein the first aftertreatment component is a hydrolysis catalyst, the second aftertreatment component is an SCR brick, and the injector is coupled with a supply of aqueous urea solution.

4. The apparatus of claim 1 wherein each of the first exhaust probe and the second exhaust probe is an FTIR probe configured to measure the exhaust species concentration.

5. The apparatus of claim 1 wherein the sectional area comprises about 50% or more of a total sectional area of the exhaust flow path.

6. The apparatus of claim 1 wherein the sectional area comprises about 100% of a total sectional area of the exhaust flow path.

7. The apparatus of claim 1 wherein the first portion of the sectional area and the second portion of the sectional area each comprises about 50% of a total sectional area of the exhaust flow path.

8. The apparatus of claim 1, wherein:
the first arm is moveable between (i) the first retracted position, in which the first exhaust probe is located adjacent to the inner surface of the housing at a first side of the housing, and (ii) the first extended position, in which the first exhaust probe is located adjacent to the inner surface of the housing at a second side of the housing, opposite the first side; and
the second arm is moveable between (i) the second retracted position, in which the second exhaust probe is located adjacent to the inner surface of the housing at a third side of the housing, and (ii) the second extended position, in which the second exhaust probe is located adjacent to the inner surface of the housing at a fourth side of the housing, opposite the third side.

9. A system comprising:
an exhaust aftertreatment system configured to receive exhaust from an internal combustion engine; and
a test device operatively coupled with the exhaust aftertreatment system, the test device including an exhaust passage configured to receive exhaust from the exhaust aftertreatment system, a first extension member extending into the exhaust passage, a first probe coupled with the first extension member and configured to measure a constituent of the exhaust, and a first actuator configured to move the first extension member, a second extension member extending into the exhaust passage, a second probe coupled with the second extension member and configured to measure a constituent of the exhaust, and a second actuator configured to move the second extension member;
wherein the system is configurable to position the first probe in a first plurality of locations in a first portion of a sectional area of the exhaust passage through movement of the first extension member without interrupting exhaust flow in the exhaust passage;
wherein the system is configurable to position the second probe in a second plurality of locations in a second portion of the sectional area of the exhaust passage through movement of the second extension member without interrupting exhaust flow in the exhaust passage;
wherein the first extension member is moveable between (i) a first retracted position, in which the first probe is located adjacent to an inner surface of a housing of the test device, and (ii) a first extended position, in which the first probe is located at a position beyond a central axis of the housing; and wherein the second extension member is moveable between (i) a second retracted position, in which the second probe is located adjacent to the inner surface of the housing, and (ii) a second extended position, in which the second probe is located at the position beyond the central axis of the housing.

10. The system of claim 9 wherein the first plurality of locations of the first probe intersect a line extending through a center point of the exhaust passage and the second plurality of locations of the second probe intersect a second line extending through the center point.

11. The system of claim 10 wherein the system is configurable to measure the constituent of the exhaust with one of the first probe and the second probe through a combination of linear movement of the first extension member, linear movement of the second extension member, and rotation of the first extension member and the second extension member relative to the exhaust flow passage.

12. The system of claim 11 wherein the linear movement and the rotation of the first extension member are effective to position the first probe in substantially any position in a first 50% of the sectional area of the exhaust passage and the linear movement and the rotation of the second extension member are effective to position the second probe in substantially any position in a second 50% of the sectional area of the exhaust passage.

13. The system of claim 12 wherein the first extension member and the second extension member are rotatable by at least 90 degrees relative to the exhaust aftertreatment system.

14. The system of claim 9, wherein:
the first arm is moveable between (i) the first retracted position, in which the first exhaust probe is located adjacent to the inner surface of the housing at a first side of the housing, and (ii) the first extended position, in which the first exhaust probe is located adjacent to the inner surface of the housing at a second side of the housing, opposite the first side; and
the second arm is moveable between (i) the second retracted position, in which the second exhaust probe is located adjacent to the inner surface of the housing at a third side of the housing, and (ii) the second extended position, in which the second exhaust probe is located adjacent to the inner surface of the housing at a fourth side of the housing, opposite the third side.

* * * * *